United States Patent
Jimenez et al.

(10) Patent No.: US 10,017,766 B2
(45) Date of Patent: Jul. 10, 2018

(54) SIRNA AND THEIR USE IN METHODS AND COMPOSITIONS FOR INHIBITING THE EXPRESSION OF THE FLAP GENE

(71) Applicant: SYLENTIS SAU, Madrid (ES)

(72) Inventors: Ana Isabel Jimenez, Madrid (ES); Covadonga Pañeda, Madrid (ES); Tamara Martinez, Madrid (ES)

(73) Assignee: SYLENTIS SAU, Madrid (ES)

( * ) Notice: Subject to any disclaimer, the term of this patent is extended or adjusted under 35 U.S.C. 154(b) by 0 days.

(21) Appl. No.: 15/030,169

(22) PCT Filed: Oct. 21, 2014

(86) PCT No.: PCT/EP2014/072500
§ 371 (c)(1),
(2) Date: Apr. 18, 2016

(87) PCT Pub. No.: WO2015/059116
PCT Pub. Date: Apr. 30, 2015

(65) Prior Publication Data
US 2016/0304867 A1 Oct. 20, 2016

(30) Foreign Application Priority Data
Oct. 22, 2013 (EP) ..................................... 13382413

(51) Int. Cl.
C12N 15/113 (2010.01)
A61K 31/713 (2006.01)

(52) U.S. Cl.
CPC ........ *C12N 15/113* (2013.01); *C12N 2310/14* (2013.01); *C12N 2310/321* (2013.01); *C12N 2310/335* (2013.01); *C12N 2310/50* (2013.01); *C12N 2320/30* (2013.01)

(58) Field of Classification Search
None
See application file for complete search history.

(56) References Cited

U.S. PATENT DOCUMENTS

| | | | | |
|---|---|---|---|---|
| 7,829,535 | B2 * | 11/2010 | O'Connor | A61K 31/405 514/16.7 |
| 2006/0094032 | A1 * | 5/2006 | Fougerolles | A61K 31/712 435/6.16 |
| 2007/0219206 | A1 * | 9/2007 | Hutchinson | C07D 401/12 514/249 |
| 2011/0269807 | A1 * | 11/2011 | Baciu | A61K 9/0051 514/406 |

FOREIGN PATENT DOCUMENTS

| | | |
|---|---|---|
| WO | WO 2004/015107 | 2/2004 |
| WO | WO 2008/030369 | 3/2008 |
| WO | WO 2008/104978 | 9/2008 |
| WO | WO 2009/105723 | 8/2009 |
| WO | WO 2011/137363 | 11/2011 |
| WO | WO 2011/148193 | 12/2011 |

OTHER PUBLICATIONS

Bair et al., "The nuclear membrane leukotriene synthetic complex is a signal integrator and transducer," Molecular Biology of the Cell, pp. 4456-4464, 2012.
Diamant et al., "The effect of MK-0591, a novel 5-lipoxygenase activating protein inhibitor, on leukotriene biosynthesis and allergen-induced airway responses in asthmatic subjects in vivo," J. Allergy Clin Immunil, 95(1), pp. 42-51.
Dixon et al., "Requirement of a 5-lipoxygenase-activating protein for leukotriene synthesis," Nature, 343, pp. 282-284, 1990.
Ferguson et al., "Crystal Structure of Inhibitor-Bound Human 5-Lipoxygenase-Activating Protein," Science, 317, pp. 510-512, 2007.
Galli et al., "IgE and mast cells in allergic disease," Nature Medicine, 18(5), pp. 693-704, 2012.
Hazouri, "Leukotrien antagonists in the treatment of allergic rhinitis and comorbidities," Revista Alergia México, 55(4), pp. 164-175, 2008, with English abstract.
Hofmann et al., "5-Lipoxygenase Inhibitors: a review of recent patents (2010-2012)," Exper. Opin. Ther. Patents, pp. 1-15, downloaded on Jun. 2013.
Ma et al., "Structural basis for 5'-end-specific recognition of guide RNA by the A. fulgidus Piwi protein," Nature, 434, pp. 666-670, 2005.
Mancini et al., "5-Lipoxygenase-activating protein is an arachidonate binding protein," FEBS, 318(3), pp. 277-281, 1993.
Musiyenko et al., "A Novel 5-Lipoxygenase-Activating Protein Inhibitor, AM679, Reduces Inflammation in the Respiratory Syncytial Virus-Infected Mouse-Eye," Clinical and Vaccine Immunology, vol. 16, No. 11, pp. 1654-1659, Nov. 1, 2009.
Plewako et al., "Increased expression of lipoxygenase enzymes during pollen season in nasal biopsies of pollen-allergic patients," Allergy, 61, pp. 725-730, 2006.
Shumilina et al., "Phosphoinositide-dependent Kinase PDK1 in the Regulation of Ca2+ Entry into Mast Cells," Cellular Physiology and Biochemistry, 26, pp. 699-706, 2010.
Tao et al, "Using siRNA Technique to Analyze the Role of 5-lipoxygenase Activating Protein in Highly Purified Glomerular Endothelial Cells," Journal of Clinical Rehabilitative Tissue Engineering Research, vol. 12, No. 2, pp. 283-288, Jan. 8, 2008.
Woods et al., "5-Lipoxygenase and 5-Lipoxygenase-activating Protein are Localized in the Nuclear Envelope of Activated Human Leukocytes," J. Exp. Med., 178, pp. 1935-1946, 1993.

(Continued)

*Primary Examiner* — Tracy Vivlemore
(74) *Attorney, Agent, or Firm* — Margaret B. Brivanlou; Kenneth H. Sonnenfeld; King & Spalding LLP

(57) ABSTRACT

The invention relates to si RNA molecules and their use in methods and pharmaceutical compositions for inhibiting the expression of the FLAP gene. The invention also relates to the use of said si RNAs molecules in the treatment and/or prevention of an eye condition characterized by increased expression and/or activity of FLAP gene, preferably said eye condition is conjunctivitis and/or an ocular allergy such as seasonal allergic conjunctivitis, perennial allergic conjunctivitis, vernal keratoconjunctivitis, atopic keratoconjunctivitis, and giant papillary conjunctivitis.

15 Claims, 13 Drawing Sheets

(56) References Cited

OTHER PUBLICATIONS

Angaji et al., "Application of RNA interference in treating human diseases," J. of Genetics, 89(4), pp. 527-537, 2010.
Bacsi et al., "Effect of pollen-mediated oxidative stress on immediate hypersensitivity reactions and late-phase inflammation in allergic conjunctivitis," J. Allergy Clin Immunol., 116(4), pp. 836-843, 2005.
Bramsen et al., "A large-scale chemical modification screen identifies design rules to generate siRNAs with high activity, high stability and low toxicity," Nucleic Acids Research, 37(9), pp. 2867-2881, 2009.
Cerutti et al., "Domains in gene silencing and cell differentiation proteins: the novel PAZ domain and redefinition of the Piwi domain," Protein Sequence Motifs, pp. 481-482, 2000.
Chang et al., "Structural Diversity Repertoire of Gene Silencing Small Interfering RNAs," Nucleic Acid Therapeutics, 21(3), pp. 125-131, 2011.
Collins et al., "Structural domains in RNAi," FEBS Lett., 579(26), pp. 5841-5849, 2005.
Deleavey et al., "Designing Chemically Modified Oligonucleotides for Targeted Gene Silencing," Chemistry & Biology, 19, pp. 937-954, 2012.
Doench et al., "Specificity of microRNA target selection in translational repression," Genes Dev., 18, pp. 504-511, 2004.
Elbashir et al., "RNA interference is mediated by 21-and 22-nucleotide RNAs," Genes & Development, 15, pp. 188-200, 2001.
Fire et al., "Potent and specific genetic interference by double-stranded RNA in Caenorhabditis elegans," Nature, 39, pp. 806-811, 1998.
Kari et al., "Updates in the treatment of ocular allergies," J. of Asthma and Allergy, 3, pp. 149-158, 2010.
Kay, "Allergy and Allergic Diseases," N. Engl. J. Med., 344(1), pp. 30-37, 2001.
Kim et al., "Synthetic dsRNA Dicer substrates enhance RNAi potency and efficacy," Nature Biotechnology, 23(2), pp. 222-226, 2005.
Kombrust et al., "Oligo Safety Working Group Exaggerated Pharmacology Subcommittee Consensus Document," Nucleic Acid Therapeutics, 23, pp. 21-28, 2013.
La Rosa et al., "Allergic conjunctivitis: a comprehensive review of the literature," Italian Journal of Pediatrics, 39, pp. 1-8, 2013.
Lewis et al., "Prediction of Mammalian MicroRNA Targets," Cell, 115, pp. 787-798, 2003.
Liu et al., "Argonaute2 is the Catalytic Engine of Mammalian RNAi," Science, 305, pp. 1437-1441, 2004.
Livak et al., "Analysis of Relative Gene Expression Data Using Real-Time Quantitative PCR and the $22^{-\Delta\Delta C_T}$ Method," Methods, 25, pp. 402-408, 2001.
Magone et al., "A Novel Murine Model of Allergic Conjunctivitis," Clinical Immunology and Immunopathology, 87(1), pp. 75-84, 1998.
Maniatis, "Separation of RNA According to Size: Electrophoresis of Glyoxylated RNA through Agarose Gels," Molecular Cloning, 5 pages, 1982.
Nykanen et al., "ATP Requirements and Small Interfering RNA Structure in the RNA Interference Pathway," Cell, 107, pp. 309-321, 2001.
Ono et al., "Allergic conjunctivitis: Update on pathophysiology and prospects for future treatment," J. Allergy Clin. Immunol., pp. 118-122, 2005.
Parrish et al., "Functional Anatomy of a dsRNA Trigger: Differential Requirement for the Two Trigger Strands in RNA Interference," Molecular Cell, 6, pp. 1077-1087, 2000.
Popescu, "Antisense-and RNA Interference-Based Therapeutics Strategies in Allergy," J. Cell. Mol. Med., 19(4), pp. 840-853, 2005.
Rand et al., "Argonaute2 Cleaves the Anti-Guide Strand of siRNA during RISC Activation," Cell, 123, pp. 621-629, 2005.
Sanghvi, "A Status Update of Modified Oligonucleotides for Chemotherapeutics Applications," Curr. Protoc. Nucleic Acid Chem., 46, pp. 4.1.1-4.1.22, 2011.
Song, et al., "Crystal Structure of Argonaute and Its Implications for RISC Slicer Activity," Science, 305, pp. 1434-1437, 2004.
Suzuki et al., "Inhibition of allergic responses by CD40 gene silencing," Allergy, 64, pp. 387-397, 2009.
Suzuki, et al., "A novel allergen-specific therapy for allergy using CD40-silenced dendritic cells," J. Allergy Clin. Immunol., pp. 737-743e6, 2010.
Walton et al., "Designing Highly Active siRNAs for Therapeutic Applications," FEBS J., 277(23), pp. 4806-4813, 2010.
Lambiase et al., "Montelukast, a Leukotriene Receptor Antagonist, in Vernal Keratoconjunctivitis Associated with Asthma," Arch. Ophthalmol., 121, pp. 615-620, 2003.

* cited by examiner

| FLAP target sequences (cDNA) | |
|---|---|
| SEQ ID NO. 1 | ATGCGTACCCCACTTTCCT |
| SEQ ID NO. 2 | GCGGGTCTACACTGCCAAC |
| SEQ ID NO. 3 | CGGGTCTACACTGCCAACC |
| SEQ ID NO. 4 | GGGTCTACACTGCCAACCA |
| SEQ ID NO. 5 | GATGCGTACCCCACTTTCC |
| SEQ ID NO. 6 | CTGATGTACTTGTTTGTGA |
| SEQ ID NO. 7 | TCATCAGCGTGGTCCAGAA |
| SEQ ID NO. 8 | TCTACACTGCCAACCAGAA |
| SEQ ID NO. 9 | CTTGCCTTTGAGCGGGTCT |
| SEQ ID NO. 10 | TTGCCTTTGAGCGGGTCTA |
| SEQ ID NO. 11 | TGCCTTTGAGCGGGTCTAC |
| SEQ ID NO. 12 | GCCTTTGAGCGGGTCTACA |
| SEQ ID NO. 13 | CCTTTGAGCGGGTCTACAC |
| SEQ ID NO. 14 | CTTTGAGCGGGTCTACACT |
| SEQ ID NO. 15 | TTTGAGCGGGTCTACACTG |
| SEQ ID NO. 16 | GAGCGGGTCTACACTGCCA |
| SEQ ID NO. 17 | AGCGGGTCTACACTGCCAA |
| SEQ ID NO. 18 | TAGATGCGTACCCCACTTT |
| SEQ ID NO. 19 | AGATGCGTACCCCACTTTC |
| SEQ ID NO. 20 | ATGCGTACCCCACTTTCCT |
| SEQ ID NO. 21 | CTGATGTACTTGTTTGTGA |
| SEQ ID NO. 22 | GGTCCAGAATGGATTCTTT |
| SEQ ID NO. 23 | CGAAAGCAGGACCCAGAAT |
| SEQ ID NO. 24 | CCGGAACACTTGCCTTTGA |
| SEQ ID NO. 25 | CAACCAGAACTGTGTAGAT |
| SEQ ID NO. 26 | CCAAGTTCCTGCTGCGTTT |
| SEQ ID NO. 27 | CGTTTGCTGGACTGATGTA |
| SEQ ID NO. 28 | CTGGACTGATGTACTTGTT |
| SEQ ID NO. 29 | GGTTACCTAGGAGAGAGAA |
| SEQ ID NO. 30 | CGTTTGCTGGACTGATGTA |
| SEQ ID NO. 31 | GTACTTGTTTGTGAGGCAA |
| SEQ ID NO. 32 | GGTCCAGAATGGATTCTTT |
| SEQ ID NO. 33 | GTACTTTGTCGGTTACCTA |
| SEQ ID NO. 34 | CATAAAGTGGAGCACGAAA |
| SEQ ID NO. 35 | AGAACTGTGTAGATGCGTA |
| SEQ ID NO. 36 | CGGTTACCTAGGAGAGAGA |
| SEQ ID NO. 37 | GCGTGGTCCAGAATGGATT |
| SEQ ID NO. 38 | GGTCCAGAATGGATTCTTT |
| SEQ ID NO. 39 | GAATGGATTCTTTGCCCAT |
| SEQ ID NO. 40 | CCCATAAAGTGGAGCACGA |
| SEQ ID NO. 41 | CCATAAAGTGGAGCACGAA |
| SEQ ID NO. 42 | CATAAAGTGGAGCACGAAA |
| SEQ ID NO. 43 | GCACGAAAGCAGGACCCAG |

FIG. 1

| SEQ ID NO. 44 | ACGAAAGCAGGACCCAGAA |
| SEQ ID NO. 45 | CGAAAGCAGGACCCAGAAT |
| SEQ ID NO. 46 | CCCAGAATGGGAGGAGCTT |
| SEQ ID NO. 47 | GGGAGGAGCTTCCAGAGGA |
| SEQ ID NO. 48 | CCAGAGGACCGGAACACTT |
| SEQ ID NO. 49 | GGACCGGAACACTTGCCTT |
| SEQ ID NO. 50 | GACCGGAACACTTGCCTTT |
| SEQ ID NO. 51 | TGCCAACCAGAACTGTGTA |
| SEQ ID NO. 52 | CAACCAGAACTGTGTAGAT |
| SEQ ID NO. 53 | AGAACTGTGTAGATGCGTA |
| SEQ ID NO. 54 | GCTCTGGTCTGCGGGGCTA |
| SEQ ID NO. 55 | GGGGCTACTTTGCAGCCAA |
| SEQ ID NO. 56 | GCTACTTTGCAGCCAAGTT |
| SEQ ID NO. 57 | GCCAAGTTCCTGCTGCGTT |
| SEQ ID NO. 58 | CCAAGTTCCTGCTGCGTTT |
| SEQ ID NO. 59 | ACTTGTTTGTGAGGCAAAA |
| SEQ ID NO. 60 | TGTTTGTGAGGCAAAAGTA |
| SEQ ID NO. 61 | CAAAAGTACTTTGTCGGTT |
| SEQ ID NO. 62 | GTACTTTGTCGGTTACCTA |
| SEQ ID NO. 63 | GGTTACCTAGGAGAGAGAA |
| SEQ ID NO. 64 | GGTTACCTAGGAGAGAGAA |
| SEQ ID NO. 65 | CGTTTGCTGGACTGATGTA |
| SEQ ID NO. 66 | CCAACCAGAACTGTGTAGA |
| SEQ ID NO. 67 | GGTCCAGAATGGATTCTTT |
| SEQ ID NO. 68 | GCTGGACTGATGTACTTGT |
| SEQ ID NO. 69 | GACTGATGTACTTGTTTGT |
| SEQ ID NO. 70 | CTGGACTGATGTACTTGTT |
| SEQ ID NO. 71 | CAACCAGAACTGTGTAGAT |
| SEQ ID NO. 72 | TGGACTGATGTACTTGTTT |
| SEQ ID NO. 73 | TCTACACTGCCAACCAGAA |
| SEQ ID NO. 74 | CATCAGCGTGGTCCAGAAT |
| SEQ ID NO. 75 | GACCGGAACACTTGCCTTT |
| SEQ ID NO. 76 | GATTCTTTGCCCATAAAGT |
| SEQ ID NO. 77 | TGTGAGGCAAAAGTACTTT |
| SEQ ID NO. 78 | TGGTCCAGAATGGATTCTT |
| SEQ ID NO. 79 | GTGGTCCAGAATGGATTCT |
| SEQ ID NO. 80 | CTGCCAACCAGAACTGTGT |
| SEQ ID NO. 81 | CTGGTCTGCGGGGCTACTT |
| SEQ ID NO. 82 | GTGAGGCAAAAGTACTTTG |
| SEQ ID NO. 83 | ACTTTGCAGCCAAGTTCCT |
| SEQ ID NO. 84 | TAGATGCGTACCCCACTTT |
| SEQ ID NO. 85 | TCTGGTCTGCGGGGCTACT |
| SEQ ID NO. 86 | GCUGGACUGAUGUACUUGU |
| SEQ ID NO. 87 | GUGGUCCAGAAUGGAUUCU |
| SEQ ID NO. 88 | CCAACCAGAACUGUGUAGA |
| SEQ ID NO. 89 | GUACUUGUUUGUGAGGCAA |

FIG. 1 Cont'd

| FLAP siRNAs | Sense strand 5'->3' | Antisense strand 5'->3' |
|---|---|---|
| SEQ ID NO. 90 | AUGCGUACCCCACUUUCCU | AGGAAAGUGGGGUACGCAU |
| SEQ ID NO. 91 | GCGGGUCUACACUGCCAAC | GUUGGCAGUGUAGACCCGC |
| SEQ ID NO. 92 | CGGGUCUACACUGCCAACC | GGUUGGCAGUGUAGACCCG |
| SEQ ID NO. 93 | GGGUCUACACUGCCAACCA | UGGUUGGCAGUGUAGACCC |
| SEQ ID NO. 94 | GAUGCGUACCCCACUUUCC | GGAAAGUGGGGUACGCAUC |
| SEQ ID NO. 95 | CUGAUGUACUUGUUUGUGA | UCACAAACAAGUACAUCAG |
| SEQ ID NO. 96 | UCAUCAGCGUGGUCCAGAA | UUCUGGACCACGCUGAUGA |
| SEQ ID NO. 97 | UCUACACUGCCAACCAGAA | UUCUGGUUGGCAGUGUAGA |
| SEQ ID NO. 98 | CUUGCCUUUGAGCGGGUCU | AGACCCGCUCAAAGGCAAG |
| SEQ ID NO. 99 | UUGCCUUUGAGCGGGUCUA | UAGACCCGCUCAAAGGCAA |
| SEQ ID NO. 100 | UGCCUUUGAGCGGGUCUAC | GUAGACCCGCUCAAAGGCA |
| SEQ ID NO. 101 | GCCUUUGAGCGGGUCUACA | UGUAGACCCGCUCAAAGGC |
| SEQ ID NO. 102 | CCUUUGAGCGGGUCUACAC | GUGUAGACCCGCUCAAAGG |
| SEQ ID NO. 103 | CUUUGAGCGGGUCUACACU | AGUGUAGACCCGCUCAAAG |
| SEQ ID NO. 104 | UUUGAGCGGGUCUACACUG | CAGUGUAGACCCGCUCAAA |
| SEQ ID NO. 105 | GAGCGGGUCUACACUGCCA | UGGCAGUGUAGACCCGCUC |
| SEQ ID NO. 106 | AGCGGGUCUACACUGCCAA | UUGGCAGUGUAGACCCGCU |
| SEQ ID NO. 107 | UAGAUGCGUACCCCACUUU | AAAGUGGGGUACGCAUCUA |
| SEQ ID NO. 108 | AGAUGCGUACCCCACUUUC | GAAAGUGGGGUACGCAUCU |
| SEQ ID NO. 109 | AUGCGUACCCCACUUUCCU | AGGAAAGUGGGGUACGCAU |
| SEQ ID NO. 110 | CUGAUGUACUUGUUUGUGA | UCACAAACAAGUACAUCAG |
| SEQ ID NO. 111 | GGUCCAGAAUGGAUUCUUU | AAAGAAUCCAUUCUGGACC |
| SEQ ID NO. 112 | CGAAAGCAGGACCCAGAAU | AUUCUGGGUCCUGCUUUCG |
| SEQ ID NO. 113 | CCGGAACACUUGCCUUUGA | UCAAAGGCAAGUGUUCCGG |
| SEQ ID NO. 114 | CAACCAGAACUGUGUAGAU | AUCUACACAGUUCUGGUUG |
| SEQ ID NO. 115 | CCAAGUUCCUGCUGCGUUU | AAACGCAGCAGGAACUUGG |
| SEQ ID NO. 116 | CGUUUGCUGGACUGAUGUA | UACAUCAGUCCAGCAAACG |
| SEQ ID NO. 117 | CUGGACUGAUGUACUUGUU | AACAAGUACAUCAGUCCAG |
| SEQ ID NO. 118 | GGUUACCUAGGAGAGAGAA | UUCUCUCUCCUAGGUAACC |
| SEQ ID NO. 119 | CGUUUGCUGGACUGAUGUA | UACAUCAGUCCAGCAAACG |
| SEQ ID NO. 120 | GUACUUGUUUGUGAGGCAA | UUGCCUCACAAACAAGUAC |
| SEQ ID NO. 121 | GGUCCAGAAUGGAUUCUUU | AAAGAAUCCAUUCUGGACC |
| SEQ ID NO. 122 | GUACUUUGUCGGUUACCUA | UAGGUAACCGACAAAGUAC |
| SEQ ID NO. 123 | CAUAAAGUGGAGCACGAAA | UUUCGUGCUCCACUUUAUG |
| SEQ ID NO. 124 | AGAACUGUGUAGAUGCGUA | UACGCAUCUACACAGUUCU |
| SEQ ID NO. 125 | CGGUUACCUAGGAGAGAGA | UCUCUCUCCUAGGUAACCG |
| SEQ ID NO. 126 | GCGUGGUCCAGAAUGGAUU | AAUCCAUUCUGGACCACGC |
| SEQ ID NO. 127 | GGUCCAGAAUGGAUUCUUU | AAAGAAUCCAUUCUGGACC |
| SEQ ID NO. 128 | GAAUGGAUUCUUUGCCCAU | AUGGGCAAAGAAUCCAUUC |
| SEQ ID NO. 129 | CCCAUAAAGUGGAGCACGA | UCGUGCUCCACUUUAUGGG |
| SEQ ID NO. 130 | CCAUAAAGUGGAGCACGAA | UUCGUGCUCCACUUUAUGG |
| SEQ ID NO. 131 | CAUAAAGUGGAGCACGAAA | UUUCGUGCUCCACUUUAUG |
| SEQ ID NO. 132 | GCACGAAAGCAGGACCCAG | CUGGGUCCUGCUUUCGUGC |

FIG. 2

| SEQ ID NO. 133 | ACGAAAGCAGGACCCAGAA | UUCUGGGUCCUGCUUUCGU |
| SEQ ID NO. 134 | CGAAAGCAGGACCCAGAAU | AUUCUGGGUCCUGCUUUCG |
| SEQ ID NO. 135 | CCCAGAAUGGGAGGAGCUU | AAGCUCCUCCCAUUCUGGG |
| SEQ ID NO. 136 | GGGAGGAGCUUCCAGAGGA | UCCUCUGGAAGCUCCUCCC |
| SEQ ID NO. 137 | CCAGAGGACCGGAACACUU | AAGGCAAGUGUUCCGGUCC |
| SEQ ID NO. 138 | GGACCGGAACACUUGCCUU | AAGGCAAGUGUUCCGGUCC |
| SEQ ID NO. 139 | GACCGGAACACUUGCCUUU | AAAGGCAAGUGUUCCGGUC |
| SEQ ID NO. 140 | UGCCAACCAGAACUGUGUA | UACACAGUUCUGGUUGGCA |
| SEQ ID NO. 141 | CAACCAGAACUGUGUAGAU | AUCUACACAGUUCUGGUUG |
| SEQ ID NO. 142 | AGAACUGUGUAGAUGCGUA | UACGCAUCUACACAGUUCU |
| SEQ ID NO. 143 | GCUCUGGUCUGCGGGGCUA | UAGCCCCGCAGACCAGAGC |
| SEQ ID NO. 144 | GGGGCUACUUUGCAGCCAA | UUGGCUGCAAAGUAGCCCC |
| SEQ ID NO. 145 | GCUACUUUGCAGCCAAGUU | AACUUGGCUGCAAAGUAGC |
| SEQ ID NO. 146 | GCCAAGUUCCUGCUGCGUU | AACGCAGCAGGAACUUGGC |
| SEQ ID NO. 147 | CCAAGUUCCUGCUGCGUUU | AAACGCAGCAGGAACUUGG |
| SEQ ID NO. 148 | ACUUGUUUGUGAGGCAAAA | UUUUGCCUCACAAACAAGU |
| SEQ ID NO. 149 | UGUUUGUGAGGCAAAAGUA | UACUUUUGCCUCACAAACA |
| SEQ ID NO. 150 | CAAAAGUACUUUGUCGGUU | AACCGACAAAGUACUUUUG |
| SEQ ID NO. 151 | GUACUUUGUCGGUUACCUA | UAGGUAACCGACAAAGUAC |
| SEQ ID NO. 152 | GGUUACCUAGGAGAGAGAA | UUCUCUCUCCUAGGUAACC |
| SEQ ID NO. 153 | GGUUACCUAGGAGAGAGAA | UUCUCUCUCCUAGGUAACC |
| SEQ ID NO. 154 | CGUUUGCUGGACUGAUGUA | UACAUCAGUCCAGCAAACG |
| SEQ ID NO. 155 | CCAACCAGAACUGUGUAGA | UCUACACAGUUCUGGUUGG |
| SEQ ID NO. 156 | GGUCCAGAAUGGAUUCUUU | AAAGAAUCCAUUCUGGACC |
| SEQ ID NO. 157 | GCUGGACUGAUGUACUUGU | ACAAGUACAUCAGUCCAGC |
| SEQ ID NO. 158 | GACUGAUGUACUUGUUUGU | ACAAACAAGUACAUCAGUC |
| SEQ ID NO. 159 | CUGGACUGAUGUACUUGUU | AACAAGUACAUCAGUCCAG |
| SEQ ID NO. 160 | CAACCAGAACUGUGUAGAU | AUCUACACAGUUCUGGUUG |
| SEQ ID NO. 161 | UGGACUGAUGUACUUGUUU | AAACAAGUACAUCAGUCCA |
| SEQ ID NO. 162 | UCUACACUGCCAACCAGAA | UUCUGGUUGGCAGUGUAGA |
| SEQ ID NO. 163 | CAUCAGCUGGUCCAGAAU | AUUCUGGACCACGCUGAUG |
| SEQ ID NO. 164 | GACCGGAACACUUGCCUUU | AAAGGCAAGUGUUCCGGUC |
| SEQ ID NO. 165 | GAUUCUUUGCCCAUAAAGU | ACUUUAUGGGCAAAGAAUC |
| SEQ ID NO. 166 | UGUGAGGCAAAAGUACUUU | AAAGUACUUUUGCCUCACA |
| SEQ ID NO. 167 | UGGUCCAGAAUGGAUUCUU | AAGAAUCCAUUCUGGACCA |
| SEQ ID NO. 168 | GUGGUCCAGAAUGGAUUCU | AGAAUCCAUUCUGGACCAC |
| SEQ ID NO. 169 | CUGCCAACCAGAACUGUGU | ACACAGUUCUGGUUGGCAG |
| SEQ ID NO. 170 | CUGGUCUGCGGGGCUACUU | AAGUAGCCCCGCAGACCAG |
| SEQ ID NO. 171 | GUGAGGCAAAAGUACUUUG | CAAAGUACUUUUGCCUCAC |
| SEQ ID NO. 172 | ACUUUGCAGCCAAGUUCCU | AGGAACUUGGCUGCAAAGU |
| SEQ ID NO. 173 | UAGAUGCGUACCCCACUUU | AAAGUGGGGUACGCAUCUA |
| SEQ ID NO. 174 | UCUGGUCUGCGGGGCUACU | AGUAGCCCCGCAGACCAGA |
| SEQ ID NO. 175 | GCUGGACUGAUGUACUUGU | CGACCUGACUACAUGAACA |
| SEQ ID NO. 176 | GUGGUCCAGAAUGGAUUCU | CACCAGGUCUUACCUAAGA |
| SEQ ID NO. 177 | CCAACCAGAACUGUGUAGA | GGUUGGUCUUGACACAUCU |
| SEQ ID NO. 178 | GUACUUGUUUGUGAGGCAA | CAUGAACAAACACUCCGUU |

FIG. 2 Cont'd

A.
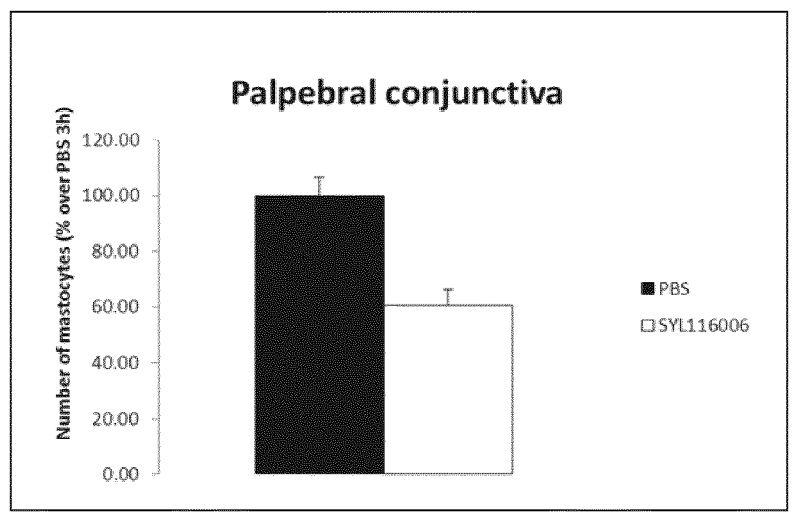
B.
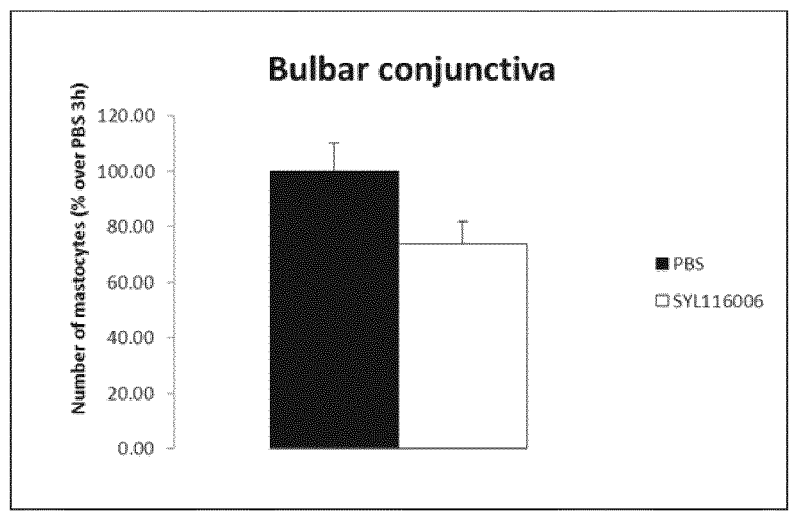
FIGURE 11

A.
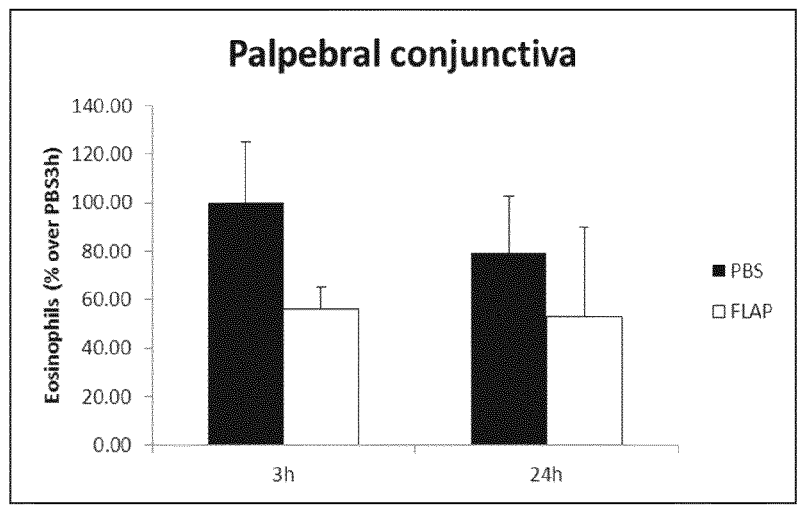
B.
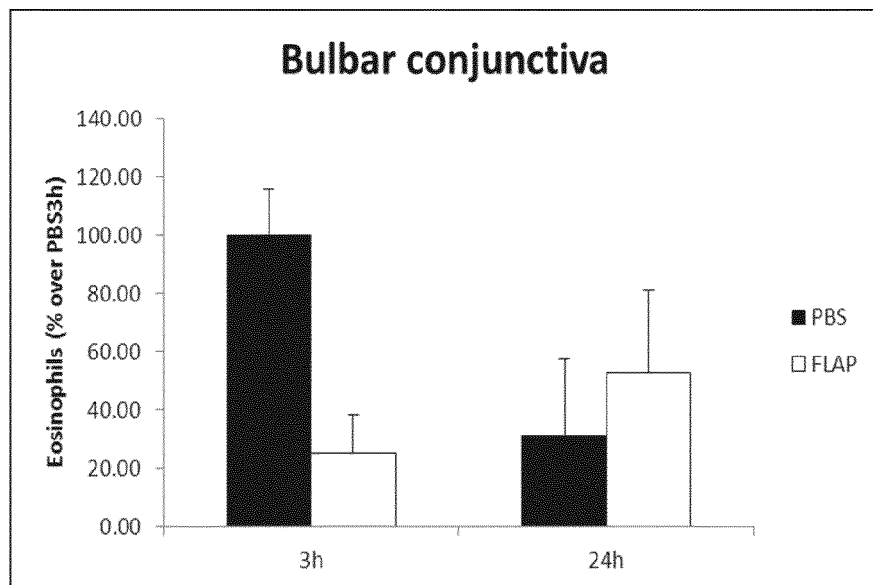
FIGURE 12

SEQUENCE LISTING

<160> NUMBER OF SEQ ID NOS: 178

<210> SEQ ID NO 1
<211> LENGTH: 19
<212> TYPE: DNA
<213> ORGANISM: Homo sapiens

<400> SEQUENCE: 1
atgcgtaccc cactttcct                                                    19

<210> SEQ ID NO 2
<211> LENGTH: 19
<212> TYPE: DNA
<213> ORGANISM: Homo sapiens

<400> SEQUENCE: 2
gcgggtctac actgccaac                                                    19

<210> SEQ ID NO 3
<211> LENGTH: 19
<212> TYPE: DNA
<213> ORGANISM: Homo sapiens

<400> SEQUENCE: 3
cgggtctaca ctgccaacc                                                    19

<210> SEQ ID NO 4
<211> LENGTH: 19
<212> TYPE: DNA
<213> ORGANISM: Homo sapiens

<400> SEQUENCE: 4
gggtctacac tgccaacca                                                    19

<210> SEQ ID NO 5
<211> LENGTH: 19
<212> TYPE: DNA
<213> ORGANISM: Homo sapiens

<400> SEQUENCE: 5
gatgcgtacc ccactttcc                                                    19

<210> SEQ ID NO 6
<211> LENGTH: 19
<212> TYPE: DNA
<213> ORGANISM: Homo sapiens

<400> SEQUENCE: 6
ctgatgtact tgtttgtga                                                    19

<210> SEQ ID NO 7
<211> LENGTH: 19
<212> TYPE: DNA
<213> ORGANISM: Homo sapiens

<400> SEQUENCE: 7
tcatcagcgt ggtccagaa                                                    19

<210> SEQ ID NO 8
<211> LENGTH: 19
<212> TYPE: DNA
<213> ORGANISM: Homo sapiens

<400> SEQUENCE: 8
tctacactgc caaccagaa                                              19

<210> SEQ ID NO 9
<211> LENGTH: 19
<212> TYPE: DNA
<213> ORGANISM: Homo sapiens

<400> SEQUENCE: 9
cttgcctttg agcgggtct                                              19

<210> SEQ ID NO 10
<211> LENGTH: 19
<212> TYPE: DNA
<213> ORGANISM: Homo sapiens

<400> SEQUENCE: 10
ttgcctttga gcgggtcta                                              19

<210> SEQ ID NO 11
<211> LENGTH: 19
<212> TYPE: DNA
<213> ORGANISM: Homo sapiens

<400> SEQUENCE: 11
tgcctttgag cgggtctac                                              19

<210> SEQ ID NO 12
<211> LENGTH: 19
<212> TYPE: DNA
<213> ORGANISM: Homo sapiens

<400> SEQUENCE: 12
gcctttgagc gggtctaca                                              19

<210> SEQ ID NO 13
<211> LENGTH: 19
<212> TYPE: DNA
<213> ORGANISM: Homo sapiens

<400> SEQUENCE: 13
cctttgagcg ggtctacac                                              19

<210> SEQ ID NO 14
<211> LENGTH: 19
<212> TYPE: DNA
<213> ORGANISM: Homo sapiens

<400> SEQUENCE: 14
ctttgagcgg gtctacact                                              19

<210> SEQ ID NO 15
<211> LENGTH: 19
<212> TYPE: DNA
<213> ORGANISM: Homo sapiens

<400> SEQUENCE: 15
tttgagcggg tctacactg                                              19

<210> SEQ ID NO 16
<211> LENGTH: 19
<212> TYPE: DNA
<213> ORGANISM: Homo sapiens

```
<400> SEQUENCE: 16
gagcgggtct acactgcca                                              19

<210> SEQ ID NO 17
<211> LENGTH: 19
<212> TYPE: DNA
<213> ORGANISM: Homo sapiens

<400> SEQUENCE: 17
agcgggtcta cactgccaa                                              19

<210> SEQ ID NO 18
<211> LENGTH: 19
<212> TYPE: DNA
<213> ORGANISM: Homo sapiens

<400> SEQUENCE: 18
tagatgcgta ccccactttt                                             19

<210> SEQ ID NO 19
<211> LENGTH: 19
<212> TYPE: DNA
<213> ORGANISM: Homo sapiens

<400> SEQUENCE: 19
agatgcgtac cccactttc                                              19

<210> SEQ ID NO 20
<211> LENGTH: 19
<212> TYPE: DNA
<213> ORGANISM: Homo sapiens

<400> SEQUENCE: 20
atgcgtaccc cactttcct                                              19

<210> SEQ ID NO 21
<211> LENGTH: 19
<212> TYPE: DNA
<213> ORGANISM: Homo sapiens

<400> SEQUENCE: 21
ctgatgtact tgtttgtga                                              19

<210> SEQ ID NO 22
<211> LENGTH: 19
<212> TYPE: DNA
<213> ORGANISM: Homo sapiens

<400> SEQUENCE: 22
ggtccagaat ggattcttt                                              19

<210> SEQ ID NO 23
<211> LENGTH: 19
<212> TYPE: DNA
<213> ORGANISM: Homo sapiens

<400> SEQUENCE: 23
cgaaagcagg acccagaat                                              19

<210> SEQ ID NO 24
<211> LENGTH: 19
<212> TYPE: DNA
<213> ORGANISM: Homo sapiens
```

```
<400> SEQUENCE: 24
ccggaacact tgcctttga                                                19

<210> SEQ ID NO 25
<211> LENGTH: 19
<212> TYPE: DNA
<213> ORGANISM: Homo sapiens

<400> SEQUENCE: 25
caaccagaac tgtgtagat                                                19

<210> SEQ ID NO 26
<211> LENGTH: 19
<212> TYPE: DNA
<213> ORGANISM: Homo sapiens

<400> SEQUENCE: 26
ccaagttcct gctgcgttt                                                19

<210> SEQ ID NO 27
<211> LENGTH: 19
<212> TYPE: DNA
<213> ORGANISM: Homo sapiens

<400> SEQUENCE: 27
cgtttgctgg actgatgta                                                19

<210> SEQ ID NO 28
<211> LENGTH: 19
<212> TYPE: DNA
<213> ORGANISM: Homo sapiens

<400> SEQUENCE: 28
ctggactgat gtacttgtt                                                19

<210> SEQ ID NO 29
<211> LENGTH: 19
<212> TYPE: DNA
<213> ORGANISM: Homo sapiens

<400> SEQUENCE: 29
ggttacctag gagagagaa                                                19

<210> SEQ ID NO 30
<211> LENGTH: 19
<212> TYPE: DNA
<213> ORGANISM: Homo sapiens

<400> SEQUENCE: 30
cgtttgctgg actgatgta                                                19

<210> SEQ ID NO 31
<211> LENGTH: 19
<212> TYPE: DNA
<213> ORGANISM: Homo sapiens

<400> SEQUENCE: 31
gtacttgttt gtgaggcaa                                                19

<210> SEQ ID NO 32
<211> LENGTH: 19
<212> TYPE: DNA
```

```
<213> ORGANISM: Homo sapiens

<400> SEQUENCE: 32
ggtccagaat ggattcttt                                                    19

<210> SEQ ID NO 33
<211> LENGTH: 19
<212> TYPE: DNA
<213> ORGANISM: Homo sapiens

<400> SEQUENCE: 33
gtactttgtc ggttaccta                                                    19

<210> SEQ ID NO 34
<211> LENGTH: 19
<212> TYPE: DNA
<213> ORGANISM: Homo sapiens

<400> SEQUENCE: 34
cataaagtgg agcacgaaa                                                    19

<210> SEQ ID NO 35
<211> LENGTH: 19
<212> TYPE: DNA
<213> ORGANISM: Homo sapiens

<400> SEQUENCE: 35
agaactgtgt agatgcgta                                                    19

<210> SEQ ID NO 36
<211> LENGTH: 19
<212> TYPE: DNA
<213> ORGANISM: Homo sapiens

<400> SEQUENCE: 36
cggttaccta ggagagaga                                                    19

<210> SEQ ID NO 37
<211> LENGTH: 19
<212> TYPE: DNA
<213> ORGANISM: Homo sapiens

<400> SEQUENCE: 37
gcgtggtcca gaatggatt                                                    19

<210> SEQ ID NO 38
<211> LENGTH: 19
<212> TYPE: DNA
<213> ORGANISM: Homo sapiens

<400> SEQUENCE: 38
ggtccagaat ggattcttt                                                    19

<210> SEQ ID NO 39
<211> LENGTH: 19
<212> TYPE: DNA
<213> ORGANISM: Homo sapiens

<400> SEQUENCE: 39
gaatggattc tttgcccat                                                    19

<210> SEQ ID NO 40
<211> LENGTH: 19
```

```
<212> TYPE: DNA
<213> ORGANISM: Homo sapiens

<400> SEQUENCE: 40
cccataaagt ggagcacga                                              19

<210> SEQ ID NO 41
<211> LENGTH: 19
<212> TYPE: DNA
<213> ORGANISM: Homo sapiens

<400> SEQUENCE: 41
ccataaagtg gagcacgaa                                              19

<210> SEQ ID NO 42
<211> LENGTH: 19
<212> TYPE: DNA
<213> ORGANISM: Homo sapiens

<400> SEQUENCE: 42
cataaagtgg agcacgaaa                                              19

<210> SEQ ID NO 43
<211> LENGTH: 19
<212> TYPE: DNA
<213> ORGANISM: Homo sapiens

<400> SEQUENCE: 43
gcacgaaagc aggacccag                                              19

<210> SEQ ID NO 44
<211> LENGTH: 19
<212> TYPE: DNA
<213> ORGANISM: Homo sapiens

<400> SEQUENCE: 44
acgaaagcag gacccagaa                                              19

<210> SEQ ID NO 45
<211> LENGTH: 19
<212> TYPE: DNA
<213> ORGANISM: Homo sapiens

<400> SEQUENCE: 45
cgaaagcagg acccagaat                                              19

<210> SEQ ID NO 46
<211> LENGTH: 19
<212> TYPE: DNA
<213> ORGANISM: Homo sapiens

<400> SEQUENCE: 46
cccagaatgg gaggagctt                                              19

<210> SEQ ID NO 47
<211> LENGTH: 19
<212> TYPE: DNA
<213> ORGANISM: Homo sapiens

<400> SEQUENCE: 47
gggaggagct tccagagga                                              19

<210> SEQ ID NO 48
```

```
<211> LENGTH: 19
<212> TYPE: DNA
<213> ORGANISM: Homo sapiens

<400> SEQUENCE: 48
ccagaggacc ggaacactt                                                   19

<210> SEQ ID NO 49
<211> LENGTH: 19
<212> TYPE: DNA
<213> ORGANISM: Homo sapiens

<400> SEQUENCE: 49
ggaccggaac acttgcctt                                                   19

<210> SEQ ID NO 50
<211> LENGTH: 19
<212> TYPE: DNA
<213> ORGANISM: Homo sapiens

<400> SEQUENCE: 50
gaccggaaca cttgccttt                                                   19

<210> SEQ ID NO 51
<211> LENGTH: 19
<212> TYPE: DNA
<213> ORGANISM: Homo sapiens

<400> SEQUENCE: 51
tgccaaccag aactgtgta                                                   19

<210> SEQ ID NO 52
<211> LENGTH: 19
<212> TYPE: DNA
<213> ORGANISM: Homo sapiens

<400> SEQUENCE: 52
caaccagaac tgtgtagat                                                   19

<210> SEQ ID NO 53
<211> LENGTH: 19
<212> TYPE: DNA
<213> ORGANISM: Homo sapiens

<400> SEQUENCE: 53
agaactgtgt agatgcgta                                                   19

<210> SEQ ID NO 54
<211> LENGTH: 19
<212> TYPE: DNA
<213> ORGANISM: Homo sapiens

<400> SEQUENCE: 54
gctctggtct gcggggcta                                                   19

<210> SEQ ID NO 55
<211> LENGTH: 19
<212> TYPE: DNA
<213> ORGANISM: Homo sapiens

<400> SEQUENCE: 55
ggggctactt tgcagccaa                                                   19
```

```
<210> SEQ ID NO 56
<211> LENGTH: 19
<212> TYPE: DNA
<213> ORGANISM: Homo sapiens

<400> SEQUENCE: 56
gctactttgc agccaagtt                                              19

<210> SEQ ID NO 57
<211> LENGTH: 19
<212> TYPE: DNA
<213> ORGANISM: Homo sapiens

<400> SEQUENCE: 57
gccaagttcc tgctgcgtt                                              19

<210> SEQ ID NO 58
<211> LENGTH: 19
<212> TYPE: DNA
<213> ORGANISM: Homo sapiens

<400> SEQUENCE: 58
ccaagttcct gctgcgttt                                              19

<210> SEQ ID NO 59
<211> LENGTH: 19
<212> TYPE: DNA
<213> ORGANISM: Homo sapiens

<400> SEQUENCE: 59
acttgtttgt gaggcaaaa                                              19

<210> SEQ ID NO 60
<211> LENGTH: 19
<212> TYPE: DNA
<213> ORGANISM: Homo sapiens

<400> SEQUENCE: 60
tgtttgtgag gcaaaagta                                              19

<210> SEQ ID NO 61
<211> LENGTH: 19
<212> TYPE: DNA
<213> ORGANISM: Homo sapiens

<400> SEQUENCE: 61
caaaagtact tgtcggtt                                               19

<210> SEQ ID NO 62
<211> LENGTH: 19
<212> TYPE: DNA
<213> ORGANISM: Homo sapiens

<400> SEQUENCE: 62
gtactttgtc ggttaccta                                              19

<210> SEQ ID NO 63
<211> LENGTH: 19
<212> TYPE: DNA
<213> ORGANISM: Homo sapiens

<400> SEQUENCE: 63
ggttacctag gagagagaa                                              19
```

```
<210> SEQ ID NO 64
<211> LENGTH: 19
<212> TYPE: DNA
<213> ORGANISM: Homo sapiens

<400> SEQUENCE: 64
ggttacctag gagagagaa                                                19

<210> SEQ ID NO 65
<211> LENGTH: 19
<212> TYPE: DNA
<213> ORGANISM: Homo sapiens

<400> SEQUENCE: 65
cgtttgctgg actgatgta                                                19

<210> SEQ ID NO 66
<211> LENGTH: 19
<212> TYPE: DNA
<213> ORGANISM: Homo sapiens

<400> SEQUENCE: 66
ccaaccagaa ctgtgtaga                                                19

<210> SEQ ID NO 67
<211> LENGTH: 19
<212> TYPE: DNA
<213> ORGANISM: Homo sapiens

<400> SEQUENCE: 67
ggtccagaat ggattcttt                                                19

<210> SEQ ID NO 68
<211> LENGTH: 19
<212> TYPE: DNA
<213> ORGANISM: Homo sapiens

<400> SEQUENCE: 68
gctggactga tgtacttgt                                                19

<210> SEQ ID NO 69
<211> LENGTH: 19
<212> TYPE: DNA
<213> ORGANISM: Homo sapiens

<400> SEQUENCE: 69
gactgatgta cttgtttgt                                                19

<210> SEQ ID NO 70
<211> LENGTH: 19
<212> TYPE: DNA
<213> ORGANISM: Homo sapiens

<400> SEQUENCE: 70
ctggactgat gtacttgtt                                                19

<210> SEQ ID NO 71
<211> LENGTH: 19
<212> TYPE: DNA
<213> ORGANISM: Homo sapiens

<400> SEQUENCE: 71
caaccagaac tgtgtagat                                                19
```

```
<210> SEQ ID NO 72
<211> LENGTH: 19
<212> TYPE: DNA
<213> ORGANISM: Homo sapiens

<400> SEQUENCE: 72
tggactgatg tacttgttt                                               19

<210> SEQ ID NO 73
<211> LENGTH: 19
<212> TYPE: DNA
<213> ORGANISM: Homo sapiens

<400> SEQUENCE: 73
tctacactgc caaccagaa                                               19

<210> SEQ ID NO 74
<211> LENGTH: 19
<212> TYPE: DNA
<213> ORGANISM: Homo sapiens

<400> SEQUENCE: 74
catcagcgtg gtccagaat                                               19

<210> SEQ ID NO 75
<211> LENGTH: 19
<212> TYPE: DNA
<213> ORGANISM: Homo sapiens

<400> SEQUENCE: 75
gaccggaaca cttgccttt                                               19

<210> SEQ ID NO 76
<211> LENGTH: 19
<212> TYPE: DNA
<213> ORGANISM: Homo sapiens

<400> SEQUENCE: 76
gattctttgc ccataaagt                                               19

<210> SEQ ID NO 77
<211> LENGTH: 19
<212> TYPE: DNA
<213> ORGANISM: Homo sapiens

<400> SEQUENCE: 77
tgtgaggcaa aagtacttt                                               19

<210> SEQ ID NO 78
<211> LENGTH: 19
<212> TYPE: DNA
<213> ORGANISM: Homo sapiens

<400> SEQUENCE: 78
tggtccagaa tggattctt                                               19

<210> SEQ ID NO 79
<211> LENGTH: 19
<212> TYPE: DNA
<213> ORGANISM: Homo sapiens

<400> SEQUENCE: 79
```
gtggtccaga atggattct                                                19

<210> SEQ ID NO 80
<211> LENGTH: 19
<212> TYPE: DNA
<213> ORGANISM: Homo sapiens

<400> SEQUENCE: 80
ctgccaacca gaactgtgt                                                19

<210> SEQ ID NO 81
<211> LENGTH: 19
<212> TYPE: DNA
<213> ORGANISM: Homo sapiens

<400> SEQUENCE: 81
ctggtctgcg gggctactt                                                19

<210> SEQ ID NO 82
<211> LENGTH: 19
<212> TYPE: DNA
<213> ORGANISM: Homo sapiens

<400> SEQUENCE: 82
gtgaggcaaa agtactttg                                                19

<210> SEQ ID NO 83
<211> LENGTH: 19
<212> TYPE: DNA
<213> ORGANISM: Homo sapiens

<400> SEQUENCE: 83
actttgcagc caagttcct                                                19

<210> SEQ ID NO 84
<211> LENGTH: 19
<212> TYPE: DNA
<213> ORGANISM: Homo sapiens

<400> SEQUENCE: 84
tagatgcgta ccccacttt                                                19

<210> SEQ ID NO 85
<211> LENGTH: 19
<212> TYPE: DNA
<213> ORGANISM: Homo sapiens

<400> SEQUENCE: 85
tctggtctgc ggggctact                                                19

<210> SEQ ID NO 86
<211> LENGTH: 19
<212> TYPE: RNA
<213> ORGANISM: Homo sapiens

<400> SEQUENCE: 86
gcuggacuga uguacuugu                                                19

<210> SEQ ID NO 87
<211> LENGTH: 19
<212> TYPE: RNA
<213> ORGANISM: Homo sapiens

<400> SEQUENCE: 87
gugguccaga auggauucu                                            19

<210> SEQ ID NO 88
<211> LENGTH: 19
<212> TYPE: RNA
<213> ORGANISM: Homo sapiens

<400> SEQUENCE: 88
ccaaccagaa cuguguaga                                            19

<210> SEQ ID NO 89
<211> LENGTH: 19
<212> TYPE: RNA
<213> ORGANISM: Homo sapiens

<400> SEQUENCE: 89
guacuuguuu gugaggcaa                                            19

<210> SEQ ID NO 90
<211> LENGTH: 19
<212> TYPE: RNA
<213> ORGANISM: Artificial Sequence
<220> FEATURE:
<223> OTHER INFORMATION: FLAP siRNA

<400> SEQUENCE: 90
augcguaccc cacuuuccu                                            19

<210> SEQ ID NO 91
<211> LENGTH: 19
<212> TYPE: RNA
<213> ORGANISM: Artificial Sequence
<220> FEATURE:
<223> OTHER INFORMATION: FLAP siRNA

<400> SEQUENCE: 91
gcgggucuac acugccaac                                            19

<210> SEQ ID NO 92
<211> LENGTH: 19
<212> TYPE: RNA
<213> ORGANISM: Artificial Sequence
<220> FEATURE:
<223> OTHER INFORMATION: FLAP siRNA

<400> SEQUENCE: 92
cgggucuaca cugccaacc                                            19

<210> SEQ ID NO 93
<211> LENGTH: 19
<212> TYPE: RNA
<213> ORGANISM: Artificial Sequence
<220> FEATURE:
<223> OTHER INFORMATION: FLAP siRNA

<400> SEQUENCE: 93
gggucuacac ugccaacca                                            19

<210> SEQ ID NO 94
<211> LENGTH: 19
<212> TYPE: RNA
<213> ORGANISM: Artificial Sequence
<220> FEATURE:
<223> OTHER INFORMATION: FLAP siRNA

```
<400> SEQUENCE: 94
gaugcguacc ccacuuucc                                                19

<210> SEQ ID NO 95
<211> LENGTH: 19
<212> TYPE: RNA
<213> ORGANISM: Artificial Sequence
<220> FEATURE:
<223> OTHER INFORMATION: FLAP siRNA

<400> SEQUENCE: 95
cugauguacu uguuuguga                                                19

<210> SEQ ID NO 96
<211> LENGTH: 19
<212> TYPE: DNA
<213> ORGANISM: Artificial Sequence
<220> FEATURE:
<223> OTHER INFORMATION: FLAP siRNA

<400> SEQUENCE: 96
gaccggaaca cttgccttt                                                19

<210> SEQ ID NO 97
<211> LENGTH: 19
<212> TYPE: RNA
<213> ORGANISM: Artificial Sequence
<220> FEATURE:
<223> OTHER INFORMATION: FLAP siRNA

<400> SEQUENCE: 97
ucuacacugc caaccagaa                                                19

<210> SEQ ID NO 98
<211> LENGTH: 19
<212> TYPE: RNA
<213> ORGANISM: Artificial Sequence
<220> FEATURE:
<223> OTHER INFORMATION: FLAP siRNA

<400> SEQUENCE: 98
cuugccuuug agcgggucu                                                19

<210> SEQ ID NO 99
<211> LENGTH: 19
<212> TYPE: RNA
<213> ORGANISM: Artificial Sequence
<220> FEATURE:
<223> OTHER INFORMATION: FLAP siRNA

<400> SEQUENCE: 99
uugccuuuga gcgggucua                                                19

<210> SEQ ID NO 100
<211> LENGTH: 19
<212> TYPE: RNA
<213> ORGANISM: Artificial Sequence
<220> FEATURE:
<223> OTHER INFORMATION: FLAP siRNA

<400> SEQUENCE: 100
ugccuuugag cgggucuac                                                19

<210> SEQ ID NO 101
<211> LENGTH: 19
```

<212> TYPE: RNA
<213> ORGANISM: Artificial Sequence
<220> FEATURE:
<223> OTHER INFORMATION: FLAP siRNA

<400> SEQUENCE: 101
gccuuugagc ggucuaca                                                    19

<210> SEQ ID NO 102
<211> LENGTH: 19
<212> TYPE: RNA
<213> ORGANISM: Artificial Sequence
<220> FEATURE:
<223> OTHER INFORMATION: FLAP siRNA

<400> SEQUENCE: 102
ccuuugagcg ggucuacac                                                   19

<210> SEQ ID NO 103
<211> LENGTH: 19
<212> TYPE: RNA
<213> ORGANISM: Artificial Sequence
<220> FEATURE:
<223> OTHER INFORMATION: FLAP siRNA

<400> SEQUENCE: 103
ccuuugagcg ggucuacac                                                   19

<210> SEQ ID NO 104
<211> LENGTH: 19
<212> TYPE: RNA
<213> ORGANISM: Artificial Sequence
<220> FEATURE:
<223> OTHER INFORMATION: FLAP siRNA

<400> SEQUENCE: 104
uuugagcggg ucuacacug                                                   19

<210> SEQ ID NO 105
<211> LENGTH: 19
<212> TYPE: RNA
<213> ORGANISM: Artificial Sequence
<220> FEATURE:
<223> OTHER INFORMATION: FLAP siRNA

<400> SEQUENCE: 105
gagcgggucu acacugcca                                                   19

<210> SEQ ID NO 106
<211> LENGTH: 19
<212> TYPE: RNA
<213> ORGANISM: Artificial Sequence
<220> FEATURE:
<223> OTHER INFORMATION: FLAP siRNA

<400> SEQUENCE: 106
agcgggucua cacugccaa                                                   19

<210> SEQ ID NO 107
<211> LENGTH: 19
<212> TYPE: RNA
<213> ORGANISM: Artificial Sequence
<220> FEATURE:
<223> OTHER INFORMATION: FLAP siRNA

<400> SEQUENCE: 107
uagaugcgua ccccacuuu                                                19

<210> SEQ ID NO 108
<211> LENGTH: 19
<212> TYPE: RNA
<213> ORGANISM: Artificial Sequence
<220> FEATURE:
<223> OTHER INFORMATION: FLAP siRNA

<400> SEQUENCE: 108
agaugcguac cccacuuuc                                                19

<210> SEQ ID NO 109
<211> LENGTH: 19
<212> TYPE: RNA
<213> ORGANISM: Artificial Sequence
<220> FEATURE:
<223> OTHER INFORMATION: FLAP siRNA

<400> SEQUENCE: 109
augcguaccc cacuuuccu                                                19

<210> SEQ ID NO 110
<211> LENGTH: 19
<212> TYPE: RNA
<213> ORGANISM: Artificial Sequence
<220> FEATURE:
<223> OTHER INFORMATION: FLAP siRNA

<400> SEQUENCE: 110
cugauguacu uguuuguga                                                19

<210> SEQ ID NO 111
<211> LENGTH: 19
<212> TYPE: RNA
<213> ORGANISM: Artificial Sequence
<220> FEATURE:
<223> OTHER INFORMATION: FLAP siRNA

<400> SEQUENCE: 111
gguccagaau ggauucuuu                                                19

<210> SEQ ID NO 112
<211> LENGTH: 19
<212> TYPE: RNA
<213> ORGANISM: Artificial Sequence
<220> FEATURE:
<223> OTHER INFORMATION: FLAP siRNA

<400> SEQUENCE: 112
cgaaagcagg acccagaau                                                19

<210> SEQ ID NO 113
<211> LENGTH: 19
<212> TYPE: RNA
<213> ORGANISM: Artificial Sequence
<220> FEATURE:
<223> OTHER INFORMATION: FLAP siRNA

<400> SEQUENCE: 113
ccggaacacu ugccuuuga                                                19

<210> SEQ ID NO 114
<211> LENGTH: 19
<212> TYPE: RNA
<213> ORGANISM: Artificial Sequence

```
<220> FEATURE:
<223> OTHER INFORMATION: FLAP siRNA

<400> SEQUENCE: 114
caaccagaac uguguagau                                                      19

<210> SEQ ID NO 115
<211> LENGTH: 19
<212> TYPE: RNA
<213> ORGANISM: Artificial Sequence
<220> FEATURE:
<223> OTHER INFORMATION: FLAP siRNA

<400> SEQUENCE: 115
ccaaguuccu gcugcguuu                                                      19

<210> SEQ ID NO 116
<211> LENGTH: 19
<212> TYPE: RNA
<213> ORGANISM: Artificial Sequence
<220> FEATURE:
<223> OTHER INFORMATION: FLAP siRNA

<400> SEQUENCE: 116
cguuugcugg acugaugua                                                      19

<210> SEQ ID NO 117
<211> LENGTH: 19
<212> TYPE: RNA
<213> ORGANISM: Artificial Sequence
<220> FEATURE:
<223> OTHER INFORMATION: FLAP siRNA

<400> SEQUENCE: 117
cuggacugau guacuuguu                                                      19

<210> SEQ ID NO 118
<211> LENGTH: 19
<212> TYPE: RNA
<213> ORGANISM: Artificial Sequence
<220> FEATURE:
<223> OTHER INFORMATION: FLAP siRNA

<400> SEQUENCE: 118
gguuaccuag gagagagaa                                                      19

<210> SEQ ID NO 119
<211> LENGTH: 19
<212> TYPE: RNA
<213> ORGANISM: Artificial Sequence
<220> FEATURE:
<223> OTHER INFORMATION: FLAP siRNA

<400> SEQUENCE: 119
cguuugcugg acugaugua                                                      19

<210> SEQ ID NO 120
<211> LENGTH: 19
<212> TYPE: RNA
<213> ORGANISM: Artificial Sequence
<220> FEATURE:
<223> OTHER INFORMATION: FLAP siRNA

<400> SEQUENCE: 120
guacuuguuu gugaggcaa                                                      19
```

```
<210> SEQ ID NO 121
<211> LENGTH: 19
<212> TYPE: RNA
<213> ORGANISM: Artificial Sequence
<220> FEATURE:
<223> OTHER INFORMATION: FLAP siRNA

<400> SEQUENCE: 121
gguccagaau ggauucuuu                                               19

<210> SEQ ID NO 122
<211> LENGTH: 19
<212> TYPE: RNA
<213> ORGANISM: Artificial Sequence
<220> FEATURE:
<223> OTHER INFORMATION: FLAP siRNA

<400> SEQUENCE: 122
guacuuuguc gguuaccua                                               19

<210> SEQ ID NO 123
<211> LENGTH: 19
<212> TYPE: RNA
<213> ORGANISM: Artificial Sequence
<220> FEATURE:
<223> OTHER INFORMATION: FLAP siRNA

<400> SEQUENCE: 123
cauaaagugg agcacgaaa                                               19

<210> SEQ ID NO 124
<211> LENGTH: 19
<212> TYPE: RNA
<213> ORGANISM: Artificial Sequence
<220> FEATURE:
<223> OTHER INFORMATION: FLAP siRNA

<400> SEQUENCE: 124
agaacugugu agaugcgua                                               19

<210> SEQ ID NO 125
<211> LENGTH: 19
<212> TYPE: RNA
<213> ORGANISM: Artificial Sequence
<220> FEATURE:
<223> OTHER INFORMATION: FLAP siRNA

<400> SEQUENCE: 125
cgguuaccua ggagagaga                                               19

<210> SEQ ID NO 126
<211> LENGTH: 19
<212> TYPE: RNA
<213> ORGANISM: Artificial Sequence
<220> FEATURE:
<223> OTHER INFORMATION: FLAP siRNA

<400> SEQUENCE: 126
gcguggucca gaauggauu                                               19

<210> SEQ ID NO 127
<211> LENGTH: 19
<212> TYPE: RNA
<213> ORGANISM: Artificial Sequence
<220> FEATURE:
<223> OTHER INFORMATION: FLAP siRNA
```

```
<400> SEQUENCE: 127
gguccagaau ggauucuuu                                               19

<210> SEQ ID NO 128
<211> LENGTH: 19
<212> TYPE: RNA
<213> ORGANISM: Artificial Sequence
<220> FEATURE:
<223> OTHER INFORMATION: FLAP siRNA

<400> SEQUENCE: 128
gaauggauuc uuugcccau                                               19

<210> SEQ ID NO 129
<211> LENGTH: 19
<212> TYPE: RNA
<213> ORGANISM: Artificial Sequence
<220> FEATURE:
<223> OTHER INFORMATION: FLAP siRNA

<400> SEQUENCE: 129
cccauaaagu ggagcacga                                               19

<210> SEQ ID NO 130
<211> LENGTH: 19
<212> TYPE: RNA
<213> ORGANISM: Artificial Sequence
<220> FEATURE:
<223> OTHER INFORMATION: FLAP siRNA

<400> SEQUENCE: 130
ccauaaagug gagcacgaa                                               19

<210> SEQ ID NO 131
<211> LENGTH: 19
<212> TYPE: RNA
<213> ORGANISM: Artificial Sequence
<220> FEATURE:
<223> OTHER INFORMATION: FLAP siRNA

<400> SEQUENCE: 131
cauaaagugg agcacgaaa                                               19

<210> SEQ ID NO 132
<211> LENGTH: 19
<212> TYPE: RNA
<213> ORGANISM: Artificial Sequence
<220> FEATURE:
<223> OTHER INFORMATION: FLAP siRNA

<400> SEQUENCE: 132
gcacgaaagc aggacccag                                               19

<210> SEQ ID NO 133
<211> LENGTH: 19
<212> TYPE: RNA
<213> ORGANISM: Artificial Sequence
<220> FEATURE:
<223> OTHER INFORMATION: FLAP siRNA

<400> SEQUENCE: 133
acgaaagcag gacccagaa                                               19

<210> SEQ ID NO 134
```

```
<211> LENGTH: 19
<212> TYPE: RNA
<213> ORGANISM: Artificial Sequence
<220> FEATURE:
<223> OTHER INFORMATION: FLAP siRNA

<400> SEQUENCE: 134
cgaaagcagg acccagaau                                               19

<210> SEQ ID NO 135
<211> LENGTH: 19
<212> TYPE: RNA
<213> ORGANISM: Artificial Sequence
<220> FEATURE:
<223> OTHER INFORMATION: FLAP siRNA

<400> SEQUENCE: 135
cccagaaugg gaggagcuu                                               19

<210> SEQ ID NO 136
<211> LENGTH: 19
<212> TYPE: RNA
<213> ORGANISM: Artificial Sequence
<220> FEATURE:
<223> OTHER INFORMATION: FLAP siRNA

<400> SEQUENCE: 136
gggaggagcu uccagagga                                               19

<210> SEQ ID NO 137
<211> LENGTH: 19
<212> TYPE: RNA
<213> ORGANISM: Artificial Sequence
<220> FEATURE:
<223> OTHER INFORMATION: FLAP siRNA

<400> SEQUENCE: 137
ccagaggacc ggaacacuu                                               19

<210> SEQ ID NO 138
<211> LENGTH: 19
<212> TYPE: RNA
<213> ORGANISM: Artificial Sequence
<220> FEATURE:
<223> OTHER INFORMATION: FLAP siRNA

<400> SEQUENCE: 138
ggaccggaac acuugccuu                                               19

<210> SEQ ID NO 139
<211> LENGTH: 19
<212> TYPE: RNA
<213> ORGANISM: Artificial Sequence
<220> FEATURE:
<223> OTHER INFORMATION: FLAP siRNA

<400> SEQUENCE: 139
gaccggaaca cuugccuuu                                               19

<210> SEQ ID NO 140
<211> LENGTH: 19
<212> TYPE: RNA
<213> ORGANISM: Artificial Sequence
<220> FEATURE:
<223> OTHER INFORMATION: FLAP siRNA

<400> SEQUENCE: 140
```
ugccaaccag aacugugua                                                    19

<210> SEQ ID NO 141
<211> LENGTH: 19
<212> TYPE: RNA
<213> ORGANISM: Artificial Sequence
<220> FEATURE:
<223> OTHER INFORMATION: FLAP siRNA

<400> SEQUENCE: 141
caaccagaac uguguagau                                                    19

<210> SEQ ID NO 142
<211> LENGTH: 19
<212> TYPE: RNA
<213> ORGANISM: Artificial Sequence
<220> FEATURE:
<223> OTHER INFORMATION: FLAP siRNA

<400> SEQUENCE: 142
agaacugugu agaugcgua                                                    19

<210> SEQ ID NO 143
<211> LENGTH: 19
<212> TYPE: RNA
<213> ORGANISM: Artificial Sequence
<220> FEATURE:
<223> OTHER INFORMATION: FLAP siRNA

<400> SEQUENCE: 143
gcucuggucu gcggggcua                                                    19

<210> SEQ ID NO 144
<211> LENGTH: 19
<212> TYPE: RNA
<213> ORGANISM: Artificial Sequence
<220> FEATURE:
<223> OTHER INFORMATION: FLAP siRNA

<400> SEQUENCE: 144
ggggcuacuu ugcagccaa                                                    19

<210> SEQ ID NO 145
<211> LENGTH: 19
<212> TYPE: RNA
<213> ORGANISM: Artificial Sequence
<220> FEATURE:
<223> OTHER INFORMATION: FLAP siRNA

<400> SEQUENCE: 145
gcuacuuugc agccaaguu                                                    19

<210> SEQ ID NO 146
<211> LENGTH: 19
<212> TYPE: RNA
<213> ORGANISM: Artificial Sequence
<220> FEATURE:
<223> OTHER INFORMATION: FLAP siRNA

<400> SEQUENCE: 146
gccaaguucc ugcugcguu                                                    19

<210> SEQ ID NO 147
<211> LENGTH: 19
<212> TYPE: RNA

<213> ORGANISM: Artificial Sequence
<220> FEATURE:
<223> OTHER INFORMATION: FLAP siRNA

<400> SEQUENCE: 147
ccaaguuccu gcugcguuu                                                    19

<210> SEQ ID NO 148
<211> LENGTH: 19
<212> TYPE: RNA
<213> ORGANISM: Artificial Sequence
<220> FEATURE:
<223> OTHER INFORMATION: FLAP siRNA

<400> SEQUENCE: 148
acuuguuugu gaggcaaaa                                                    19

<210> SEQ ID NO 149
<211> LENGTH: 19
<212> TYPE: RNA
<213> ORGANISM: Artificial Sequence
<220> FEATURE:
<223> OTHER INFORMATION: FLAP siRNA

<400> SEQUENCE: 149
uguuugugag gcaaaagua                                                    19

<210> SEQ ID NO 150
<211> LENGTH: 19
<212> TYPE: RNA
<213> ORGANISM: Artificial Sequence
<220> FEATURE:
<223> OTHER INFORMATION: FLAP siRNA

<400> SEQUENCE: 150
caaaaguacu uugucgguu                                                    19

<210> SEQ ID NO 151
<211> LENGTH: 19
<212> TYPE: RNA
<213> ORGANISM: Artificial Sequence
<220> FEATURE:
<223> OTHER INFORMATION: FLAP siRNA

<400> SEQUENCE: 151
guacuuuguc gguuaccua                                                    19

<210> SEQ ID NO 152
<211> LENGTH: 19
<212> TYPE: RNA
<213> ORGANISM: Artificial Sequence
<220> FEATURE:
<223> OTHER INFORMATION: FLAP siRNA

<400> SEQUENCE: 152
gguuaccuag gagagagaa                                                    19

<210> SEQ ID NO 153
<211> LENGTH: 19
<212> TYPE: RNA
<213> ORGANISM: Artificial Sequence
<220> FEATURE:
<223> OTHER INFORMATION: FLAP siRNA

<400> SEQUENCE: 153
gguuaccuag gagagagaa                                                    19

<210> SEQ ID NO 154
<211> LENGTH: 19
<212> TYPE: RNA
<213> ORGANISM: Artificial Sequence
<220> FEATURE:
<223> OTHER INFORMATION: FLAP siRNA

<400> SEQUENCE: 154
cguuugcugg acugaugua                                              19

<210> SEQ ID NO 155
<211> LENGTH: 19
<212> TYPE: RNA
<213> ORGANISM: Artificial Sequence
<220> FEATURE:
<223> OTHER INFORMATION: FLAP siRNA

<400> SEQUENCE: 155
ccaaccagaa cuguguaga                                              19

<210> SEQ ID NO 156
<211> LENGTH: 19
<212> TYPE: RNA
<213> ORGANISM: Artificial Sequence
<220> FEATURE:
<223> OTHER INFORMATION: FLAP siRNA

<400> SEQUENCE: 156
gguccagaau ggauucuuu                                              19

<210> SEQ ID NO 157
<211> LENGTH: 19
<212> TYPE: RNA
<213> ORGANISM: Artificial Sequence
<220> FEATURE:
<223> OTHER INFORMATION: FLAP siRNA

<400> SEQUENCE: 157
gcuggacuga uguacuugu                                              19

<210> SEQ ID NO 158
<211> LENGTH: 19
<212> TYPE: RNA
<213> ORGANISM: Artificial Sequence
<220> FEATURE:
<223> OTHER INFORMATION: FLAP siRNA

<400> SEQUENCE: 158
gacugaugua cuuguuugu                                              19

<210> SEQ ID NO 159
<211> LENGTH: 19
<212> TYPE: RNA
<213> ORGANISM: Artificial Sequence
<220> FEATURE:
<223> OTHER INFORMATION: FLAP siRNA

<400> SEQUENCE: 159
cuggacugau guacuuguu                                              19

<210> SEQ ID NO 160
<211> LENGTH: 19
<212> TYPE: RNA
<213> ORGANISM: Artificial Sequence
<220> FEATURE:

<223> OTHER INFORMATION: FLAP siRNA

<400> SEQUENCE: 160
caaccagaac uguguagau                                              19

<210> SEQ ID NO 161
<211> LENGTH: 19
<212> TYPE: RNA
<213> ORGANISM: Artificial Sequence
<220> FEATURE:
<223> OTHER INFORMATION: FLAP siRNA

<400> SEQUENCE: 161
uggacugaug uacuuguuu                                              19

<210> SEQ ID NO 162
<211> LENGTH: 19
<212> TYPE: RNA
<213> ORGANISM: Artificial Sequence
<220> FEATURE:
<223> OTHER INFORMATION: FLAP siRNA

<400> SEQUENCE: 162
ucuacacugc caaccagaa                                              19

<210> SEQ ID NO 163
<211> LENGTH: 19
<212> TYPE: RNA
<213> ORGANISM: Artificial Sequence
<220> FEATURE:
<223> OTHER INFORMATION: FLAP siRNA

<400> SEQUENCE: 163
caucagcgug guccagaau                                              19

<210> SEQ ID NO 164
<211> LENGTH: 19
<212> TYPE: RNA
<213> ORGANISM: Artificial Sequence
<220> FEATURE:
<223> OTHER INFORMATION: FLAP siRNA

<400> SEQUENCE: 164
gaccggaaca cuugccuuu                                              19

<210> SEQ ID NO 165
<211> LENGTH: 19
<212> TYPE: RNA
<213> ORGANISM: Artificial Sequence
<220> FEATURE:
<223> OTHER INFORMATION: FLAP siRNA

<400> SEQUENCE: 165
gauucuuugc ccauaaagu                                              19

<210> SEQ ID NO 166
<211> LENGTH: 19
<212> TYPE: RNA
<213> ORGANISM: Artificial Sequence
<220> FEATURE:
<223> OTHER INFORMATION: FLAP siRNA

<400> SEQUENCE: 166
ugugaggcaa aaguacuuu                                              19

```
<210> SEQ ID NO 167
<211> LENGTH: 19
<212> TYPE: RNA
<213> ORGANISM: Artificial Sequence
<220> FEATURE:
<223> OTHER INFORMATION: FLAP siRNA

<400> SEQUENCE: 167
ugguccagaa uggauucuu                                                      19

<210> SEQ ID NO 168
<211> LENGTH: 19
<212> TYPE: RNA
<213> ORGANISM: Artificial Sequence
<220> FEATURE:
<223> OTHER INFORMATION: FLAP siRNA

<400> SEQUENCE: 168
gugguccaga auggauucu                                                      19

<210> SEQ ID NO 169
<211> LENGTH: 19
<212> TYPE: RNA
<213> ORGANISM: Artificial Sequence
<220> FEATURE:
<223> OTHER INFORMATION: FLAP siRNA

<400> SEQUENCE: 169
cugccaacca gaacugugu                                                      19

<210> SEQ ID NO 170
<211> LENGTH: 19
<212> TYPE: RNA
<213> ORGANISM: Artificial Sequence
<220> FEATURE:
<223> OTHER INFORMATION: FLAP siRNA

<400> SEQUENCE: 170
cuggucugcg gggcuacuu                                                      19

<210> SEQ ID NO 171
<211> LENGTH: 19
<212> TYPE: RNA
<213> ORGANISM: Artificial Sequence
<220> FEATURE:
<223> OTHER INFORMATION: FLAP siRNA

<400> SEQUENCE: 171
gugaggcaaa aguacuuug                                                      19

<210> SEQ ID NO 172
<211> LENGTH: 19
<212> TYPE: RNA
<213> ORGANISM: Artificial Sequence
<220> FEATURE:
<223> OTHER INFORMATION: FLAP siRNA

<400> SEQUENCE: 172
acuuugcagc caaguuccu                                                      19

<210> SEQ ID NO 173
<211> LENGTH: 19
<212> TYPE: RNA
<213> ORGANISM: Artificial Sequence
<220> FEATURE:
<223> OTHER INFORMATION: FLAP siRNA
```

```
<400> SEQUENCE: 173
uagaugcgua ccccacuuu                                               19

<210> SEQ ID NO 174
<211> LENGTH: 19
<212> TYPE: RNA
<213> ORGANISM: Artificial Sequence
<220> FEATURE:
<223> OTHER INFORMATION: FLAP siRNA

<400> SEQUENCE: 174
ucuggucugc ggggcuacu                                               19

<210> SEQ ID NO 175
<211> LENGTH: 19
<212> TYPE: RNA
<213> ORGANISM: Artificial Sequence
<220> FEATURE:
<223> OTHER INFORMATION: FLAP siRNA

<400> SEQUENCE: 175
gcuggacuga uguacuugu                                               19

<210> SEQ ID NO 176
<211> LENGTH: 19
<212> TYPE: RNA
<213> ORGANISM: Artificial Sequence
<220> FEATURE:
<223> OTHER INFORMATION: FLAP siRNA

<400> SEQUENCE: 176
gugguccaga auggauucu                                               19

<210> SEQ ID NO 177
<211> LENGTH: 19
<212> TYPE: RNA
<213> ORGANISM: Artificial Sequence
<220> FEATURE:
<223> OTHER INFORMATION: FLAP siRNA

<400> SEQUENCE: 177
ccaaccagaa cuguguaga                                               19

<210> SEQ ID NO 178
<211> LENGTH: 19
<212> TYPE: RNA
<213> ORGANISM: Artificial Sequence
<220> FEATURE:
<223> OTHER INFORMATION: FLAP siRNA

<400> SEQUENCE: 178
guacuuguuu gugaggcaa                                               19
```

SIRNA AND THEIR USE IN METHODS AND COMPOSITIONS FOR INHIBITING THE EXPRESSION OF THE FLAP GENE

FIELD OF THE INVENTION

The present invention relates to the field of siRNA products and their use in methods and compositions for the treatment and/or prevention of eye conditions, and more particularly for the treatment and/or prevention of eye conditions such as conjunctivitis and/or ocular allergy, related to high levels of expression and or activity of FLAP.

BACKGROUND OF THE INVENTION

RNA interference (RNAi) is a naturally occurring post-transcriptional regulatory mechanism present in most eukaryotic cells that uses small double stranded RNA (dsRNA) molecules to direct homology-dependent gene silencing. Its discovery by Fire and Mello in the worm *C. elegans* {Fire, 1998} was awarded the Nobel Prize in 2006. Shortly after its first description, RNAi was also shown to occur in mammalian cells, not through long dsRNAs but by means of double-stranded small interfering RNAs (siRNAs) 21 nucleotides long {Elbashir, 2001}.

The process of RNA interference is thought to be an evolutionarily-conserved cellular defence mechanism used to prevent the expression of foreign genes and is commonly shared by diverse phyla and flora, where it is called post-transcriptional gene silencing. Since the discovery of the RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins, 2005} and its activity leads to the processing of the long double stranded RNAs into 21-24 nucleotide double stranded siR-NAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir, 2001} upon adenosine-triphosphate (ATP)-dependent unwinding of the double-stranded siRNA molecule through an RNA helicase activity {Nykanen, 2001}. The catalytic activity of RISC, which leads to mRNA degradation, is mediated by the endonuclease Argonaute 2 (AGO2) {Liu, 2004; Song, 2004}. AGO2 belongs to the highly conserved Argonaute family of proteins. Argonaute proteins are ~100 KDa highly basic proteins that contain two common domains, namely PIWI and PAZ domains {Cerutti, 2000}. The PIWI domain is crucial for the interaction with Dicer and contains the nuclease activity responsible for the cleavage of mRNAs {Song, 2004}. AGO2 uses one strand of the siRNA duplex as a guide to find messenger RNAs containing complementary sequences and cleaves the phosphodiester backbone between bases 10 and 11 relative to the guide strand's 5' end {Elbashir, 2001}. An important step during the activation of RISC is the cleavage of the sense or passenger strand by AGO2, removing this strand from the complex {Rand, 2005}. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule {Ma, 2005; Doench 2004; Lewis, 2003}. Once the mRNA has been cleaved, due to the presence of unprotected RNA ends in the fragments the mRNA is further cleaved and degraded by intracellular nucleases and will no longer be translated into proteins while RISC will be recycled for subsequent rounds. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA. RNAi has been applied in biomedical research such as treatment for HIV, viral hepatitis, cardiovascular and cerebrovascular diseases, metabolic disease, neurodegenerative disorders and cancer {Angaji S A et al 2010}.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies, algorithms and/or improvements have been published since then. siRNA selection approaches have become more sophisticated as mechanistic details have emerged, in addition further analysis of existing and new data can provide additional insights into further refinement of these approaches {Walton S P et al 2010}. Alternatively, several recent studies reported the design and analysis of novel RNAi-triggering structures distinct from the classical 19+2 siRNA structure and which do not conform to the key features of classical siRNA in terms of overhang, length, or symmetry, discussing the flexibility of the RNAi machinery in mammalian cells {Chang C I et al 2011}.

Also, a lot of effort has been put into enhancing siRNA stability as this is perceived as one of the main obstacles for therapy based on siRNA, given the ubiquitous nature of RNAses in biological fluids. Another inherent problem of siRNA molecules is their immunogenicity, whereby siRNAs have been found to induce unspecific activation of the innate immune system. The knockdown of unintended genes (mR-NAs) is a well-known side effect of siRNA-mediated gene silencing. It is caused as a result of partial complementarity between the siRNA and mRNAs other than the intended target and causes off-target effects (OTEs) from genes having sequence complementarity to either siRNA strand. One of the main strategies followed for stability enhancement and OTE reduction has been the use of modified nucleotides such as 2'-O-methyl nucleotides, 2'-amino nucleotides, or nucleotides containing 2'-O or 4'-C methylene bridges. Also, the modification of the ribonucleotide backbone connecting adjacent nucleotides has been described, mainly by the introduction of phosphorothioate modified nucleotides. It seems that enhanced stability and/or reduction of immunogenicity are often inversely proportional to efficacy {Parrish, 2000}, and only a certain number, positions and/or combinations of modified nucleotides may result in a stable and/or non-immunogenic silencing compound. As this is an important hurdle for siRNA-based treatments, different studies have been published which describe certain modification patterns showing good results, examples of such include EP1527176, WO2008/050329, WO2008/104978 or WO2009/044392, although many more may be found in the literature {Sanghvi Y S. 2011; Deleavey et al 2012}.

Allergic diseases are characterized by an overreaction of the human immune system to a foreign protein substance ("allergen") that is eaten, breathed into the lungs, injected or touched. Allergies have a genetic component. If only one parent has allergies of any type, chances are 1 in 3 that each child will have an allergy. If both parents have allergies, it is much more likely (7 in 10) that their children will have allergies. There are no cures for allergies; however they can be managed with proper prevention and treatment.

About 30% of people worldwide suffer from allergic symptoms and 40-80% of them have symptoms in the eyes {Key B. 2001}. Allergic diseases affecting the eyes or ocular allergies constitute a heterogenic group of diseases with a very broad spectrum of clinical manifestations. An ocular allergy usually occurs when the conjunctiva (membrane covering the eye and the lining of the eyelid) reacts to an allergen. An ocular allergy can happen independently or in conjunction with other allergy symptoms (such as rhinitis or asthma).

Basic and clinical research has provided a better understanding of the cells, mediators, and immunologic events which occur in ocular allergy. The eye, particularly the conjunctiva, has a relatively large number of mast cells. When allergens are present they can bind to immunoglobulin, IgE, in the FcεRI receptors on the surface of these mast cells and trigger their activation and release of mediators of allergy (a process known as degranulation). Degranulation releases mast cell components, including histamine, prostaglandins, tryptase and leukotrienes, into the environment outside the mast cell. Through a variety of mechanisms these components produce the signs and symptoms of the ocular allergy. The activation of the mast cells of the allergic inflammation is frequently designated as an acute phase response or early phase of the ocular allergy. The acute phase response can progress to a late phase response characterized by recruitment of inflammatory cells to the site of the allergic inflammation, for example as an influx of eosinophils and neutrophils into the conjunctiva.

Ocular allergy represents one of the most common conditions encountered by allergist and ophthalmologists. Ocular allergy is usually associated with the following symptoms and signs: conjunctivitis, blepharitis, blepharoconjuntivitis or keratoconjunctivitis. The eye becomes red and itchy and there occurs lacrimation and slight discharge. Severe cases may also show eye burning sensation, pain and photophobia.

Allergic diseases affecting the eyes include mild forms such as seasonal allergic conjunctivitis (SAC) and perennial allergic conjunctivitis (PAC); and more severe manifestations such as vernal keratoconjunctivitis (VKC); atopic keratoconjunctivitis (AKC) and giant papillary conjunctivitis (GPC). The latter ones can be associated with complications such as corneal damage and may cause vision loss. SAC and PAC are commonly IgE-mast cell mediated hypersensitivity reaction to external allergens; whereas AKC and VKC are characterized by chronic inflammation involving several immune cell types. SAC and PAC allergens, with the help of antigen presenting cells (APCs), trigger a Th2-predominant immune response that induces B cells to release IgE. Activation of the allergic response usually involves infiltration and degranulation of mast cells.

SAC is the most common allergic disease in the eye, usually caused by allergens like airborne pollen, dust, and animal dander. The signs and symptoms usually occur during the spring and summer, and generally abate during the winter months. Itching, redness and swelling of the conjunctiva are the most characteristic symptoms, but also tearing, burning sensation, and photophobia. In most cases, SAC is not serious. However, it may be very disturbing to patients because it can affect their quality of life and can have significant socioeconomic impact {Kari O. and Saari K M 2010}.

PAC is the second most common allergic disease in the eye, usually caused by animals and mites. The symptoms and signs are much the same as in SAC, the difference is the specific allergens to which the patient is allergic and that PAC can occur throughout the year with exposure to perennial allergens. PAC affects all age groups but mostly young and middle-aged people of both sexes. In addition, PAC is often connected to dry eye syndrome.

SAC and PAC are the most common forms of ocular allergies. Estimates vary, but these types of allergy are said to affect at least 15-20% of the general population. SAC and PAC are often underdiagnosed and consequently under-treated. In SAC and PAC allergen induced local release of IgE prompts degranulation of mast cells in Ca2+ dependent mechanism. IgE-activated mast cells liberate preformed inflammatory mediators such as histamine and leukotriene 4 that are the first mediators of the allergic response. These mediators attract eosinophils that infiltrate the region amplifying the allergic response.

VKC is a relatively rare chronic allergic inflammation of the ocular surface that mainly affects children and young adolescents. Main symptoms are itching, redness, swelling, discharge and photophobia. The most characteristic sign is giant papillae in the upper tarsal conjunctiva.

AKC is a bilateral chronic inflammatory disease of the ocular surface and eyelid. The most characteristic sign are eczematous lesions on the eyelid which are itchy. It is not unusual for AKC patients to have cataract surgery at a young age {Kari O. and Saari K M 2010}.

GPC is an inflammatory disease characterized by papillary hypertrophy of the superior tarsal conjunctiva. GPC is caused by inert substances rather than allergens. When these irritative stimuli are removed the conjunctival papillary changes resolve. Protein deposits on the surface of the contact lens could become antigenic and stimulate the production of IgE {La Rosa M. et al 2013}.

Current treatments for ocular allergy include non-pharmacologic and pharmacologic strategies. Avoidance of the antigen is the primary behavioural modification for all types of ocular allergies. Artificial tear substitutes provide a barrier function and help to improve the first-line defence at the level of the conjunctiva mucosa. When non-pharmacologic strategies do not provide adequate symptom relief, pharmacologic treatments may be applied.

The mainstay of the management of ocular allergy involves the use of anti-allergic therapeutic agents such as antihistamine, dual-action or combination treatments and mast cell stabilizers. Topical antihistamines (such as Emedastine and Levocabastine) competitively and reversibly block histamine receptors and relieve itching and redness, but only for a short time. Antihistamines do not affect other proinflammatory mediators which remain inhibited. A limited duration of action necessitates frequent dosing and topical antihistamines may be irritating to the eye, especially with prolonged use.

Combination treatments using decongestants (such as oxymetazoline, tetrahydrozoline, and naphazonline) in combination with antihistamines act as vasoconstrictors but are known to sting or burn on instillation. Other adverse events include mydriasis and rebound hyperemia, rendering these combination treatments more suitable for short-term relief. In addition, these drugs are not recommended for use in patients with narrow-angle glaucoma. Mast cell stabilizers (such as cromoglycate, lodoxamide, nedocromil) have a mechanism of action that is unclear. They do not relieve existing symptoms and can be used only on a prophylactic basis to prevent mast cell degranulation with subsequent exposure to the allergen. They require a loading period during which they must be applied before the antigen exposure {La Rosa M. et al 2013}.

When the above mentioned anti-allergic drugs do not allow adequate control of the allergic inflammatory process, anti-inflammatory agents are used. Corticosteroids remain among the most potent pharmacologic agents used in the more severe variants of ocular allergy {La Rosa M. et al 2013}. However, steroidal drugs can have side effects that threaten the overall health of the patient. Chronic administration of corticosteroids can lead to drug-induced osteoporosis by suppressing intestinal calcium absorption and inhibiting bone formation. Other adverse side effects of chronic administration of corticosteroids include hypertension, hyperglycemia, hyperlipidemia (increased levels of triglycerides) and hypercholesterolemia (increased levels of cholesterol) because of the effects of these drugs on the body metabolic processes. It is also known that certain corticosteroids have a greater potential for elevating intraocular pressure ("IOP") than other compounds in this class. For example, it is known that prednisolone, which is a very potent ocular anti-inflammatory agent, has a greater tendency to elevate IOP than fluorometholone, which has moderate ocular anti-inflammatory activity. It is also known that the risk of IOP elevations associated with the topical ophthalmic use of corticosteroids increases over time. In other words, the chronic (i.e., long-term) use of these agents increases the risk of significant IOP elevations. Therefore, corticosteroids may not be appropriate for the long-term treatment of ocular allergies. In addition, chronic use of corticosteroids is contraindicated due to an increased risk for the development of cataracts and glaucoma {Ono S J, and Abelson M B, 2005}.

Allergy immunotherapy is useful in reducing the response to allergens, but its role in allergic conjunctivitis has not been proven. The main objective of this treatment is to induce clinical tolerance to the specific allergen. The therapy is administered subcutaneously in progressively increasing doses to remain below the threshold of a clinical reaction. Sublingual immunotherapy (SLIT) is considered an alternative to subcutaneous allergy immunotherapy and is administered orally under the tongue, but long-term results with SLIT are not yet available. Most of the trials with this form of therapy have been for allergic rhinitis. In general, immune responses to allergen administration are not predictive of the effectiveness of the therapy and the therapy itself can produce systemic reactions, the incidence and severity of which vary dependent of the type of allergen administered {La Rosa M. et al 2013}.

In addition, the majority of newer ophthalmic anti-allergic agents have limited durations of action and twice daily dosing is required. A topical preparation with a longer duration of action would be advantageous because it may be instilled once daily. Thus, new therapies that can offer advantages in areas such as efficacy and duration of action, while offering similar safety profiles than traditional ophthalmic anti-allergic agents, are needed.

RNA interference-based therapies have been pointed out as having the potential to satisfy unmet needs in allergy treatment {Popescu F D. 2005}. It has been demonstrated that systemic administration of CD40 siRNA in mice sensitized with an allergen is capable of attenuating nasal allergic symptoms through inhibition of dendritic cell and B cell functions and generation of regulatory T cells {Suzuki M. et al 2009}. In addition, siRNA-based allergen-specific therapy for allergic rhinitis has also been developed by using CD40-silenced and allergen-pulsed dendritic cells {Suzuki M et al 2010}.

Leukotrienes (LT) are proinflammatory lipid signalling molecules synthetized by the conversion of arachidonic acid (AA) to leukotriene A4 (LTA4) by action of the 5-lipoxygenase (5-LO) in the presence of 5-lipooxygenase-activating protein (FLAP). In response to allergens, breakdown of AA increases local production of LT. LT are very potent chemoattractants of mast cells, PMNs, monocytes and certain subsets of T cells, amplifying the allergic response.

FLAP is also known as ALOX5AP. FLAP is a protein usually associated to membranes. It can be found in the nuclear membrane {Woods J. W. et al. 1993}, the endoplasmic reticulum, and the membrane of internal vesicles. In the cytoplasm it is frequently associated to the interior of the plasmatic membrane {Mancini J. A. et al 1993}. FLAP functions as a membrane anchor for 5-LO. FLAP structure consists of 4 transmembrane alpha helices forming a barrel about 60 A high and 36 A wide {Ferguson A D et al 2007}. Inhibitors of FLAP impede translocation of 5-LO from the cytoplasm to the cell membrane and inhibit 5-LO activation. Alternatively spliced transcript variants encoding different isoforms have been identified for FLAP gene.

AA is a polyunsaturated lipid that has important functions as a structural component in biomembranes but also acts as a mediator of physiological signals when released from phospholipids. AA is the precursor of several lipid mediators, among these mediators are LT which are formed by the action of 5-LO in the presence of FLAP {Dixon R A, et al. 1990}. The first reaction in the synthesis of LT is the conversion of AA to leukotriene A4 (LTA4) which serves as precursor for all other LT. Inhibition of either 5-LO or FLAP has been shown to inhibit synthesis of LT altogether and allergen-induced responses {Diamant Z, et al. 1995; Bair A M, et al. 2012}.

Initiation of the allergy reaction starts with the binding of the allergen to the IgE molecules in the FcεRI receptors of mast cells. The activation of FcεRI triggers a change in mast cells, allowing entrance of calcium from the extracellular compartment. This entrance of calcium to the mast cells mobilizes calcium stores within the cells inducing liberation of pre-synthesized mediators and activation of phospholipase A2 (PLA2) to release AA and platelet activating factor from phospholipids. Subsequent breakdown of AA increases the concentration of LT, prostaglandins (PG) and tromboxanes. These newly synthetized mediators contribute to the amplification of the allergy response and attract inflammatory cells to the allergy site leading to the late phase of the allergy reaction {Galli S J, and Tsai M. 2012}.

LTs are inflammatory mediators playing a pathophysiological role in different diseases like asthma, allergic rhinitis as well as cardiovascular diseases and certain types of cancer. In recent years, considerable evidence has accumulated indicating that the 5-LO pathway, which catalyzes the formation of LTs, plays a role in development of allergic diseases such as asthma and a variety of inflammatory disorders {Hofmann B. et al 2013}.

During pollen season, it has been demonstrated that the number of mast cells and cells expressing 5-LO and LTA4 h are higher in seasonal allergic rhinitis (SAR) patients allergic to birch or grass than in healthy controls (P=0.02; P=0.01; P=0.03 respectively) {Plewako H et al 2006}. In addition, it has been also indicated that the inhibition of FLAP directs the inhibition of LT synthesis for the treatment of allergic rhinitis and comorbid diseases like rhinosinusitis and nasal polyposis {Sacre et al 2008}.

Therefore, it is likely that an important part of the production of LT in allergic responses is mediated by FLAP activation. WO2009/048547, WO2008/030369 and EP1071710 (MERCK) describe novel molecules that act as potent inhibitors of FLAP for the treatment of atherosclerosis, asthma, chronic obstructive pulmonary disease, allergies and allergic reactions such as allergic rhinitis, contact dermatitis, and allergic conjunctivitis.

WO2011137363 (ALLERGAN, INC.) describes a compound that inhibits or reduces 5-LO activity by inhibiting FLAP for the treatment of age-related macular degeneration (AMD) or ocular ischemic disease. In further or alternative embodiments, the FLAP inhibitor may be a siRNA.

WO2007/047207, WO2007/056228 and WO2008/097930 (AMIRA PHARMACEUTICALS, INC) describe FLAP modulators, inhibitors and/or antagonists for treating diseases in which the activity of FLAP directly, or indirectly, causes at least one symptom of the disease or condition, including ocular inflammation and allergic conjunctivitis, vernal keratoconjunctivitis, and papillary conjunctivitis. In further or alternative embodiments, the FLAP inhibitor may be a siRNA.

SUMMARY OF THE INVENTION

The present invention provides improved products for reducing FLAP expression and consequently ocular inflammation in ocular allergies. The advantage of treating ocular allergies with siRNA products versus traditional anti-allergic therapeutic agents and allergy immunotherapeutic drugs is that treatments based on siRNA should have a longer-lasting effect. This is due to the fact that once the effector molecule is no longer present, the cell will have to synthesise new protein from scratch; whereas traditional treatments would leave the levels of said protein intact.

Ocular allergies appear to be on the rise worldwide. Particularly in industrialized nations, environmental pollution is widely considered a major contributor to the heightened sensitivity of allergic individuals. In addition to worsening emissions pollution, studies have also pointed to a global increase in airborne allergens. Still another consideration is that residents of poorer countries are less likely to seek treatment for ocular allergies, a factor which may keep the reported incidence of the disease artificially low in underdeveloped countries.

Asthma and Allergy Foundation in America (AAFA) indicated that the US annual cost of allergies is estimated to be nearly $14.5 billion. They estimated 50 million Americans suffer from all types of allergies (1 in 5 Americans) including indoor/outdoor, food & drug, latex, insect, skin and eye allergies. US allergy prevalence overall has been increasing since the early 1980s across all age, sex and racial groups.

Despite geographic peculiarities, physicians from around the world find common ground in their criteria for choosing an appropriate treatment course. These criteria include efficacy, safety, and convenience of dosing and comfort of administration for the patient, according to specialists from several countries. Therefore, with an increasing number of patients complaining of a range of ocular allergic symptoms worldwide, finding the optimal treatment is every day both more complex and more interesting.

DESCRIPTION OF THE DRAWINGS

FIG. 1: shows short fragments of the target gene sequence FLAP chosen as the target sequences of the siRNAs of the present invention.

FIG. 2: shows oligonucleotide sequences for siRNA molecules of the present invention targeting FLAP encompassed by the present invention. The SEQ ID NOs given in the Figure refer to the sense (5'→3') strand; typically siRNAs will be administered as dsRNAs, so will include both the sense strand and its complement antisense strand. SEQ ID NO. 90 to SEQ ID NO. 178 are siRNAs targeting SEQ ID NO. 1 to SEQ ID NO. 75, respectively. Generally, an siRNA will include the sense and antisense strand, and may also include 3' dinucleotide overhangs (for example, dTdT). However, this is not essential.

FIG. 11: Infiltration of mast cells in palpebral and bulbar conjunctiva in response to treatment with SEQ ID NO. 90 (SYL116006) in a mouse model of ragweed pollen induced allergy. A) Infiltration of mast cells in palpebral conjunctiva expressed as percentage of number of mast cells observed in PBS treated samples 3 h after treatment. B) Infiltration of mast cells in bulbar conjunctiva expressed as percentage of number of mast cells observed in PBS treated samples 3 h after treatment.

FIG. 12: Infiltration of eosinophils in palpebral and bulbar conjunctiva in response to treatment with SEQ ID NO. 90 (SYL116006) in a mouse model of ragweed pollen induced allergy. A) Infiltration of eosinophils in palpebral conjunctiva expressed as percentage of number of mast cells observed in PBS treated samples 3 h after treatment. B)

Eosinophil infiltration in bulbar conjunctiva expressed as percentage of number of eosinophils observed in PBS treated samples 3 h after treatment.

Figure 13:
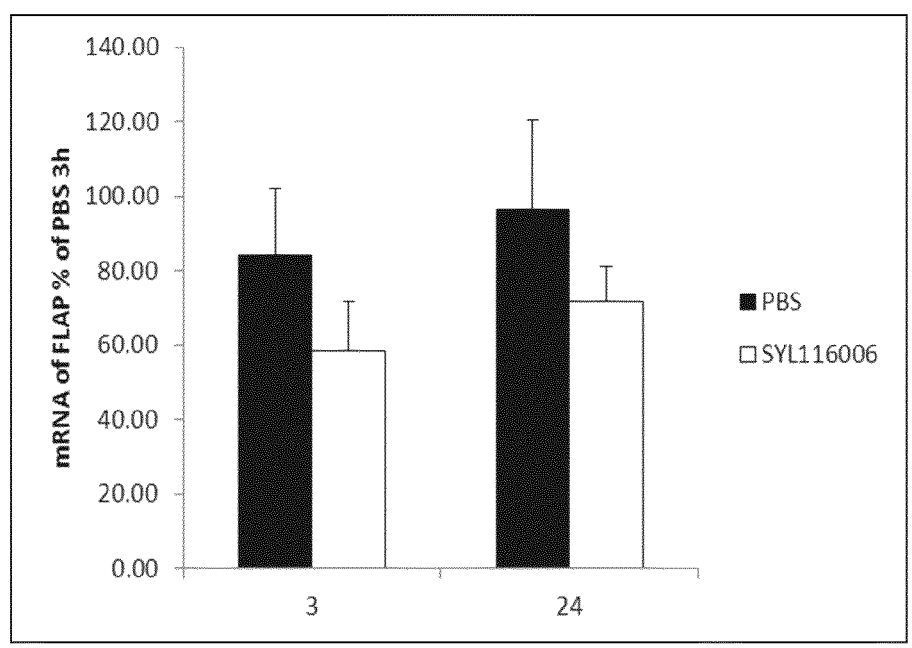

FIG. 13: FLAP expression in response to treatment with SEQ ID NO. 90 (SYL116006), a siRNA designed to silence FLAP, in a mouse model of ragweed pollen induced-allergy.

Figure 14:
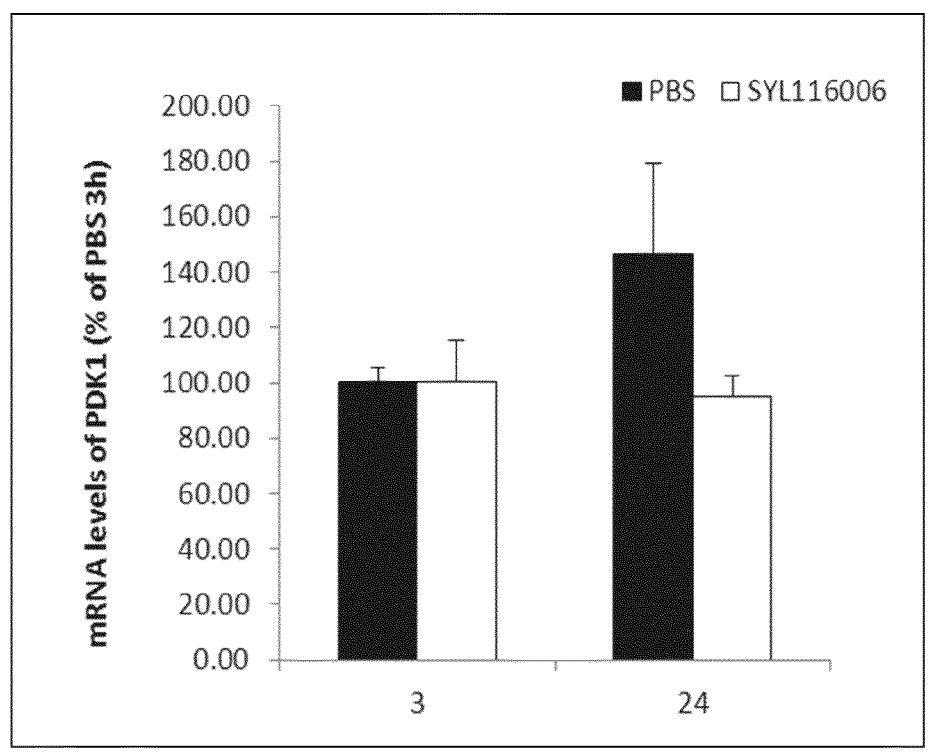

FIG. 14: PDK1 expression in response to treatment with SEQ ID NO. 90 (SYL116006), a siRNA designed to silence FLAP, in a mouse model of ragweed pollen induced-allergy.

DETAILED DESCRIPTION OF THE INVENTION

In a first aspect, the present invention relates to the provision of an siRNA molecule for use as a medicament, preferably in the treatment and/or prevention of an eye condition characterised by increased expression and/or activity of FLAP, wherein said molecule specifically targets a sequence selected from the group consisting of: SEQ ID NO. 1-SEQ ID NO. 89 and reduces expression of the FLAP gene when introduced in a cell. Preferably the target sequence is selected from the group consisting of SEQ ID NO. 1-SEQ ID NO. 20, more preferably the group consisting of SEQ ID NO. 1-SEQ ID NO. 8, and even more preferably the target sequence comprises or consists of SEQ ID NO. 1.

A gene is "targeted" by a siRNA according to the present invention when, for example, the siRNA molecule selectively decreases or inhibits the expression of the gene. The phrase "selectively decrease or inhibit" as used herein encompasses siRNAs that affect expression of one gene, in this case FLAP. Alternatively, a siRNA targets a gene when (one strand of) the siRNA hybridizes under stringent conditions to the gene transcript, i.e. its mRNA. Hybridizing "under stringent conditions" means annealing to the target mRNA region under standard conditions, e.g., high temperature and/or low salt content which tend to disfavour hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389.

Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

The target sequence as defined above is described as a target DNA sequence as used for definition of transcript variants in databases used for the purposes of designing siRNAs, whereas the specific compounds to be used will be RNA sequences defined as such.

An expert in the field can access any target gene sequence through public data bases. For example, the GenBank Accession Number corresponding to human FLAP mRNA is NM_001204406 (Gene ID: 241). Homologous GenBank Accession Number corresponding to mouse FLAP mRNA is NM_009663 (Gene ID: 11690). Furthermore, ENSEMBL (MBL-EBI/Wellcome Trust Sanger Institute) has the following FLAP human and mouse Accession Numbers: ENSG00000132965 and ENSMUSG00000060063, respectively.

The GenBank Accession Numbers corresponding to two FLAP transcripts produced by alternative splicing are: NP_001191335.1 (Accession Numbers: NM_001204406.1, GI:324711028), and NP_001620.2 (Accession Numbers: NM_001629.3, GI:324711027). Furthermore, ENSEMBL (MBL-EBI/Wellcome Trust Sanger Institute) has 2 further FLAP transcripts published: ENST00000380490 and ENST00000479597.

Said preferred target region identified by the present invention comprises or consists of at least one sequence selected from the group consisting of SEQ ID NO. 1-SEQ ID NO. 89.

In a preferred embodiment, said preferred target region comprises or consists of at least one sequence selected from the group consisting of SEQ ID NO. 1-SEQ ID NO. 20. SEQ ID NO. 1 presents 100% homology between the following species: *Homo sapiens, Mus musculus, Canis lupus familiaris*, and *Rattus norvegicus*. SEQ ID NO. 2-SEQ ID NO. 8 present 100=homology between the following species: *Homo sapiens, Mus musculus*, and *Canis lupus familiaris*.

In another preferred embodiment, said preferred target region comprises or consists of at least one sequence selected from the group consisting of SEQ ID NO. 1-SEQ ID NO. 8.

In the RNAi field, when in vitro studies demonstrated that a human siRNA is not able to induce knock down of the animal model gene, a surrogate compound (animal-active analogue) is synthetized in order to analyze the efficacy of the siRNA in the relevant animal model. This surrogate is designed against the same region as the human siRNA, thus the two siRNAs have the same sequence except for a few nucleotides, depending on the homology between the human and the rabbit target gene. This approach has been widely used for development of other oligonucleotides, specifically for toxicology studies {Kornbrust D. et al. 2013}.

In a more preferred embodiment, said preferred target region comprises or consists of SEQ ID NO. 1 (5'-ATGCGTACCCCACTTTCCT-3').

Consequently, a siRNA according to the aspects of the present invention will preferably comprise a double stranded RNA molecule, whose antisense strand will comprise an RNA sequence substantially complementary to at least one sequence selected from the group consisting of SEQ ID NO. 1-SEQ ID NO. 89, and whose sense strand will comprise an RNA sequence complementary to the antisense strand, wherein both strands are hybridised by standard base pairing between nucleotides. More preferably, a siRNA according to aspects of the present invention will preferably comprise a double stranded RNA molecule, whose antisense strand will comprise an RNA sequence substantially complementary to selected from the group consisting of SEQ ID NO. 1-SEQ ID NO. 8, and even more preferably consisting of SEQ ID NO. 1.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 85%, 86%, 87%, 88%, 89%, 90%, 91%, 92%, 93%, 94%, 95%, 96%, 97%, 98% or 99% complementarity to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule. In a preferred embodiment, the antisense siRNA strand is 100% complementary to the target mRNA sequence, and the sense strand is 100% complementary to the antisense strand over the double stranded portion of the siRNA. The siRNA may also include unpaired overhangs, for example, 3' dinucleotide overhangs, preferably dTdT.

In a preferred embodiment, said eye condition identified by the present invention is an ocular allergy and/or ocular conjunctivitis. More preferably, said eye condition is selected from seasonal allergic conjunctivitis, perennial allergic conjunctivitis, vernal keratoconjunctivitis, atopic keratoconjunctivitis, giant papillary conjunctivitis, dry eye syndrome and combinations thereof.

As is known from the state of the art, many different structures have been proposed to achieve RNA interference. Generally these double stranded molecules are from about 19 to about 25 nucleotides in length, and include blunt-ended structures as well as those with overhangs. Overhangs have been described to be advantageous and may be present on the 5' ends or on the 3' ends of either strand as they reduce recognition by RNAses and imitate Dicer's natural substrate. Some authors recommend including overhangs on both 3' ends of the molecules, whereas others consider one overhang to be sufficient. Others have described the use of blunt-ended structures with specific modification patterns (EP 1527176, WO 2005/062937, WO 2008/104978, EP 2322617, EP 2348133, US 2013/0130377, and many others).

Overhangs may be comprised of between 1 and 5 nucleotides; typically overhangs are made up of dinucleotides. Classical molecules used in the field, comprise a 19 nucleotide double stranded molecule which further comprises 3' dinucleotide overhangs preferably comprising deoxynucleotides as taught in initial studies by Tuschl (WO02/44321). These overhangs are said to further enhance resistance to nuclease (RNase) degradation. Later, Kim et al 2005 describe that 21-mer products (containing dinucleotide overhangs) are necessary for loading onto RISC. Further, Bramsen et al. 2009 describe the introduction of possible destabilizing modifications to the overhangs to further increase silencing efficiency.

As such, a preferred embodiment of the various aspects of the present invention refers to siRNA molecules targeting at least one sequence selected from the group consisting of SEQ ID NO. 1-SEQ ID NO. 89 which comprise at least one overhang. More preferably, said siRNA molecules target at least one sequence selected from the group consisting of SEQ ID NO. 1-SEQ ID NO. 8, and even more preferably consisting of SEQ ID NO. 1.

Where the invention relates to an siRNA molecule targeting at least one sequence selected from SEQ ID NO. 1 to SEQ ID NO. 89, the siRNA will include an antisense strand of equivalent length and complementary to the target, and a sense strand of equivalent length and complementary to the antisense strand. The antisense and sense strands may further include additional bases which are not complementary to the other strand or the target, and/or which are not paired in the double stranded portion of the siRNA. For example, SEQ ID NO 1 is a 19 nucleotide sequence; the siRNA may include a 19 bp double stranded region over this portion of sequence identity, and dinucleotide overhangs.

A preferred embodiment of the various aspects of the present invention refers to siRNA molecules targeting at least one sequence selected from the group consisting of SEQ ID NO. 1-SEQ ID NO. 89, wherein each strand of the double-stranded siRNA molecules is about 18 to about 28 or more (e.g., about 18, 19, 20, 21, 22, 23, 24, 25, 26, 27, or 28 or more) nucleotides long.

Another preferred embodiment of the various aspects of the present invention refers to siRNA molecules of 18-28 nucleotides long or more and comprising a nucleotide sequence selected from the group consisting of SEQ ID NO. 90-SEQ ID NO. 178. More preferably, the double-stranded siRNA molecules are at least 19 nucleotides long and selected from the group consisting of SEQ ID NO. 90-SEQ ID NO. 178.

Another alternative embodiment of the various aspects of the present invention provides blunt-ended molecules.

Further, a preferred embodiment of the present invention relates to an siRNA comprising or consisting of a 19 nucleotide double-stranded structure targeting at least one sequence selected from the group consisting of SEQ ID NO. 1-SEQ ID NO. 89. More preferably, the siRNA comprising or consisting of a 19 nucleotide double-stranded structure targeting at least one sequence selected from the group consisting of SEQ ID NO. 1-SEQ ID NO. 8, and even more preferably consisting of SEQ ID NO. 1.

A particular embodiment of the present invention relates to a 19 nucleotide double-stranded blunt-ended siRNA targeted against at least one sequence selected from the group consisting of SEQ ID NO. 1-SEQ ID NO. 89. More preferably, the siRNA is targeted against at least one sequence selected from the group consisting of SEQ ID NO. 1-SEQ ID NO. 8, and even more preferably consisting of SEQ ID NO. 1. In a further particular embodiment this compound comprises or consists of at least one sequence selected from the group consisting of SEQ ID NO. 90-SEQ ID NO. 178. In a further preferred embodiment, the antisense strand of this siRNA is at least 80%, preferably at least 90%, complementary to at least one sequence selected from the group consisting of SEQ ID NO. 90-SEQ ID NO. 109.

In a preferred embodiment, this compound comprises or consists of at least one sequence selected from the group consisting of SEQ ID NO. 90-SEQ ID NO. 97.

In a more preferred embodiment, this compound comprises or consists of SEQ ID NO. 90 (5'-AUGCGUAC-CCCACUUUCCU-3'), corresponding to sense strand of our referenced compound named SYL116006.

Furthermore, as described in the section termed background of the art, an important issue with siRNA molecules is their instability in biological fluids due to the ubiquitous nature of RNAses. Consequently, the use of many different chemical modifications to nucleotides has been described with the purpose of enhancing compound stability.

Another inherent problem of siRNA molecules is their immunogenicity, whereby siRNAs have been found to induce unspecific activation of the innate immune system, including up-regulation of certain cytokines, e.g. type I and/or type II interferon as well as IL-12, IL-6 and/or TNF-alpha production. The origin of these effects is thought to be activation of Toll-like receptors such as TLR7, TLR8 and/or TLR3 by siRNA.

Both of these effects, recognition by RNases and immunogenicity, have also been described to be sequence-dependent.

Some of the chemical modifications which enhance compound stability by decreasing susceptibility to RNAses are also able to reduce induction of immune recognition of subsequent response. However, insertion of chemically modified nucleotides in a siRNA may also result in decreased silencing efficacy as described in the previous section, and hence must be approached with caution.

Consequently, in a preferred embodiment of the various aspects of the present invention, the siRNA further comprises at least one nucleotide with a chemical modification.

Preferred chemical modifications which enhance stability and reduce immunogenic effects include 2'-O-methyl nucleotides, 2'-fluoro nucleotides, 2'-amino nucleotides, 2'-deoxy nucleotides, or nucleotides containing 2'-O or 4'-C methylene bridges. Others preferred chemical modifications for exonuclease protection include ExoEndoLight (EEL): modification of all pyrimidines in the sense strand to 2'-O-methyl residues, and modifications of all pyrimidines in a 5'-UA-3' or 5'-CA-3' motif in the antisense strand. In addition, position 1 of the sense strand can also be changed to 2'-O-methyl, preventing 5'-phosphorylation of the sense strand and thus increasing specificity of the siRNA by further inactivating the sense strand. In addition, the sense strand can also include a 2'-O-methyl modification in position 14, because 2'-O-Me at this position further inactivates the sense strand and therefore increases specificity of the siRNAs. Others preferred chemical modifications for exonuclease protection include Methyl-Fluoro (MEF): exo protection alternating 2'-fluoro and 2'-O-methyl modifications starting (5'-end) with a 2'-F on the sense strand and starting with 2'-O-Me on the antisense strand. In addition, position 1 of the sense strand can also be changed to 2'-O-Me and position 1 of the antisense strand to 2'-F (as this can efficiently be 5'-phosphorylated). Also, modification of the ribonucleotide backbone connecting adjacent nucleotides can be made by the introduction of phosphorothioate modified nucleotides. A further preferred chemical modification within the meaning of the present invention relates to the substitution of uracyl ribonucleotides with deoxythymidine (deoxyribonucleotides). In another preferred embodiment of the present invention, the at least one chemically modified nucleotide is on the sense strand, on the antisense strand or on both strands of the siRNA.

siRNA molecules as described above may be delivered to the cell interior in their native structure using methods known in the art. For example, when studying in vitro gene silencing, these compounds are administered using standard transfection reagents. To achieve effects in vivo these compounds may also be administered naked or using delivery enhancing agents such as for example liposomes, conjugation with a specific moiety, etc. although many different alternatives are known in the art, and are used differently depending on the desired target site within the body.

Alternatively, siRNA molecules of the various aspects of the invention can be expressed within cells from eukaryotic promoters. Recombinant vectors capable of expressing the siRNA molecules can be delivered and persist in target cells. Alternatively, vectors can be used that provide for transient expression of nucleic acid molecules. Such vectors can be repeatedly administered as necessary. Once expressed, the siRNA molecule interacts with the target mRNA and generates an RNA interfering response. The siRNA molecules produced in this manner are often termed shRNA (short hairpin RNA), as their sense and antisense strands are joined by a small loop of nucleotides. Delivery of siRNA molecule expressing vectors can be systemic, such as by intravenous or intra-muscular administration, by administration to target cells ex-planted from a subject followed by reintroduction into the subject, or by any other means that would allow for introduction into the desired target cell.

A further aspect of the invention relates to the use of siRNA targeting at least one sequence selected from the group consisting of SEQ ID NO. 1-SEQ ID NO. 89 in the preparation of a medicament for use in a method of treatment of an eye condition characterised by increased expression and/or activity of FLAP. More preferably, said at least one sequence is selected from the group consisting of SEQ ID NO. 1-SEQ ID NO. 8, and even more preferably said at least one sequence consists of SEQ ID NO. 1. The method comprises inhibiting expression of FLAP in a patient. The term inhibition is used to indicate a decrease or downregulation of expression or activity. Preferably, the eye condition is an ocular allergy and/or conjunctivitis. In one embodiment, the eye condition is selected from the group comprising seasonal allergic conjunctivitis, perennial allergic conjunctivitis, vernal keratoconjunctivitis, atopic keratoconjunctivitis, dry eye syndrome and combinations thereof.

Also provided is a method of treatment of an eye condition characterised by increased expression and/or activity of FLAP. The method comprises inhibiting expression of FLAP in a patient. The method may comprise administering siRNA targeting at least one sequence selected from the group consisting of SEQ ID NO. 1-SEQ ID NO. 89 More preferably, said at least one sequence is selected from the group consisting of SEQ ID NO. 1-SEQ ID NO. 8, and even more preferably said at least one sequence consists of SEQ ID NO. 1.

In some countries, the combination of chronic allergic conjunctivitis and dry eye syndrome is quite common. The increasing dry eye problem is due to common artificial climatization, indoor and outdoor pollutants and to other unknown reasons. Patients with dry eye syndrome are more prone to suffer from ocular allergies since the tear film is an important barrier in preventing allergens from coming into contact with mast cells.

Therapeutic treatment with siRNAs directed against FLAP mRNA is expected to be beneficial over small molecule topical ocular drops by increasing the length of time that effect is observed, thereby allowing less frequent dosing and greater patient compliance. This is especially important in cases such as ocular allergies, comprising but not limited to vernal keratoconjunctivitis, atopic keratoconjunctivitis, and giant papillary conjunctivitis, as they are often chronic conditions. In addition, siRNA-based treatments allow the use of so called "undruggable targets" such as intracellular proteins like FLAP as therapeutic targets.

Bearing in mind the preparation of such a medicament, the siRNA of the various aspects of the present invention may be formulated as a pharmaceutical composition. Preferably, the compositions and formulations of said siRNAs may be administered topically to the organ of interest. In an even more preferred embodiment they may be formulated for topical administration to the eye, preferably to the corneal surface of the eye. Application to the corneal surface may, for example be in the form of eye drops, a gel, lotion, cream or ocular inserts. Other administration forms to the eye may include injection into the eye.

A further preferred embodiment of the various aspects of the present invention relates to an siRNA specifically targeting at least one sequence selected from the group consisting of SEQ ID NO. 1-SEQ ID NO. 89 as described in the preceding paragraphs, for use as a medicament for the treatment of an eye condition characterised by increased expression and/or activity of FLAP. More preferably, said at least one sequence is selected from the group consisting of SEQ ID NO. 1-SEQ ID NO. 8, and even more preferably said at least one sequence consists of SEQ ID NO. 1. As described above, it may be an siRNA comprising or consisting of a 19 nucleotide double-stranded structure targeting at least one sequence selected from the group consisting of SEQ ID NO. 1-SEQ ID NO. 89. This siRNA may be blunt-ended. Preferably, the siRNA comprises or consists of at least one sequence selected from the group consisting of SEQ ID NO. 90-SEQ ID NO. 178.

Within the context of the present invention, to "specifically target" a sequence the siRNA of the invention preferably comprises at least the same seed sequence. Thus, any sequence according to the invention that specifically targets at least one sequence selected from the group consisting of SEQ ID NO. 1-SEQ ID NO. 89 is preferably identical in positions 2-8 of the antisense strand. More preferably, said at least one sequence is selected from the group consisting of SEQ ID NO. 1-SEQ ID NO. 8, and even more preferably said at least one sequence consists of SEQ ID NO. 1.

Notwithstanding the above, the siRNAs of the various aspects of the present invention may be used to silence FLAP expression in tissues other than the eye. Consequently, said siRNAs should be formulated accordingly.

For example, a siRNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In one embodiment of the present invention, the siRNA molecule is delivered through a cell-specific siRNA carrier that combines components of the hepatitis B virus and liposomes. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. The preferred compositions of the invention are aqueous solutions, specifically saline solutions such as phosphate-buffered saline (PBS) with a pH range of about 7.0 to about 7.4, preferably with a pH of 7.2±0.5.

A siRNA molecule of the invention may be complexed with membrane disruptive agents and/or a cationic lipid or helper lipid molecule.

Delivery systems which may be used with the invention include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e. g., fatty acids, fatty acid esters, fatty alcohols and amino acids), and hydrophilic polymers (e. g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) a disease state. The pharmaceutically effective dose generally depends on the type of disease, the composition used, the route of administration, the type of mammal being treated, the physical characteristics of the specific mammal under consideration, concurrent medication, and other factors that those skilled in the medical arts will recognize.

A therapeutically effective amount may also refer to the amount of a siRNA sufficient to delay or minimize the onset of an eye disorder associated with ocular allergy. A therapeutically effective amount may also refer to the amount of the therapeutic agent that provides a therapeutic benefit in the treatment or management of an eye disorder associated with ocular allergy. Further, a therapeutically effective amount with respect to a siRNA of the invention means that amount of therapeutic agent alone, or in combination with other therapies, that provides a therapeutic benefit in the treatment or management of an eye disorder associated with ocular allergy. Used in connection with an amount of a siRNA of the invention, the term can encompass an amount that improves overall therapy, reduces or avoids unwanted effects, or enhances the therapeutic efficacy of or synergizes with another therapeutic agent.

A therapeutic benefit in the treatment or management of an eye disorder such as ocular allergy is the sustained decrease in allergic symptoms. Given that siRNA will decrease the levels of FLAP within the cell, once the treatment stops the cell must re-synthesise new proteins. As such therapies based on siRNA treatments will have a more sustained effect. This is considered a significant enhancement of the therapeutic efficacy.

An additional benefit of using siRNA is the minimum probability of side effects or acute toxicity issues derived from its presence in systemic circulation, often associated with different eyedrop-based treatments. This is due to the fact that when the compound enters the bloodstream, it will be rapidly degraded by RNAses present in the blood.

On the other hand, the fact that the siRNA molecule can be marketed in single dose vials means addition of antimicrobial preservatives to the formulation can be avoided. Preservatives are present in the majority of formulations on the market today. These preservatives can produce intolerance in some patients, making it necessary to stop the treatment. Both issues are especially important when bearing in mind that conditions such as ocular allergies, comprising but not limited to vernal keratoconjunctivitis, atopic keratoconjunctivitis, and giant papillary conjunctivitis, are often chronic and therefore so is the treatment.

One of the preferred administration routes is topical, by instillation directly to the eye, preferably using eye drops. As described above, therapeutic treatment with siRNAs directed against FLAP mRNA is expected to be beneficial over small molecule topical ocular drops by increasing the length of time that the effect is observed, thereby allowing less frequent dosing and greater patient compliance.

However, as explained above, administration routes other than directly to the eye can also be used. The precise dosage and administration schedule to be employed in the formulation will also depend on the route of administration. A skilled person would understand that the precise dosage and administration schedule to be employed also depends on the seriousness of the disorder, and should be decided according to the judgment of the practitioner and each patient's circumstances. It is also understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The formulations or siRNA of the invention and described herein can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example *arachis* oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agent. The pharmaceutical compositions or siRNA of the invention and described herein can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

In preferred embodiments, the compositions of the invention are formulated in a solution, preferably a buffered saline solution such as PBS, or a gel for topical administration to the eye, such as, for example, in the form of eyedrops. In such embodiments, the formulations may be cationic emulsions and/or contain biopolymers including, but not limited to, poly(lactide-co-glycolide), carbopol, hyaluronic acid and polyacrylic acid.

The nucleic acid molecules of the invention can also be administered in the form of suppositories, e. g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

As such, a further preferred embodiment of the present invention relates to a pharmaceutical composition wherein said composition comprises at least an siRNA targeting at least one sequence selected from the group consisting of SEQ ID NO. 1-SEQ ID NO. 89, as has been described in the preceding paragraphs. More preferably, said at least one sequence is selected from the group consisting of SEQ ID NO. 1-SEQ ID NO. 8, and even more preferably said at least one sequence consists of SEQ ID NO. 1.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

As used herein the terms "ocular allergy" refers to an allergic disorder of the ocular surface caused by increased expression and/or activity of FLAP. It may also be called allergic conjunctivitis". Ocular allergy includes a wide variety of pathological conditions including but not limited to: seasonal allergic conjunctivitis (SAC), perennial allergic conjunctivitis (PAC), vernal keratoconjunctivitis (VKC), atopic keratoconjunctivitis (AKC), and giant papillary conjunctivitis (GPC).

As used herein the terms "conjunctivitis" refers to an inflammation of the conjunctiva. It is also called pink eye or madras eye in India. It is commonly due to an infection (usually viral, but sometimes bacterial) or an allergic reaction.

"Clinical symptoms" of ocular allergy include but are not limited to ocular itching, ocular redness, swelling of the eyelids, chemosis, tearing, and nasal inflammation, nasal congestion, rhinorrhea, nasal pruritis and ear/palate pruritis, and sneezing. It is preferred that the present invention treats or prevents at least two clinical symptoms, more preferably at least three, even more preferably more than four.

The term "patient," as used herein, refers to animals, including mammals, preferably humans.

As used herein the term "allergen" refers to any antigenic substance in the environment that is capable of producing immediate hypersensitivity (allergy). The list of known allergens includes plant pollens, spores of mold, animal dander, house dust, foods, feathers, dyes, soaps, detergents, cosmetics, plastics, and drugs. Allergens can enter the body by being inhaled, swallowed, touched, or injected. Airborne allergens are allergens that are light enough to be carried through air currents, for example but not limited to, pollen or spores.

The term "allergic conjunctivitis" in the present invention is understood as inflammation of the conjunctiva caused by an allergic reaction. The conjunctiva is a thin membrane that covers the eye. When an allergen irritates the conjunctiva, common symptoms that occur in the eye include: redness (mainly due to vasodilation of the peripheral small blood vessels), ocular itching, eyelid swelling, increased lacrimation, photophobia, watery discharge, and foreign body sensation (with pain). Symptoms are usually worse for patients when the weather is warm and dry, whereas cooler temperatures and rain tend to assuage symptoms.

The term "blepharitis" in the present invention is understood as a chronic inflammation of the eyelid.

The term "blepharoconjunctivitis" in the present invention is understood as the simultaneous occurrence of two separate eye conditions: blepharitis and conjunctivitis. Blepharitis affects the outer eyelids, while conjunctivitis occurs in the conjunctiva.

The term "keratoconjunctivitis" in the present invention is understood as the inflammation of the cornea and conjunctiva.

The invention is further described in the following non-limiting examples.

EXAMPLES

0. Materials
   Mouse PDK1 Probe: Taqman Gene Expression Assay Mm00554306_m1
   18S Endogenous control: Taqman Gene Expression Assay. Hs99999901_s1.
   Multiscribe Reverse Transcriptase 50 U/ml (Applied Biosystems P/N 4311235).
   RNAse inhibitor 20 U/µl (Applied Biosystems P/N N8080119).
   TaqMan 2× Universal Master Mix.
   Taqman gene expression assay Hs00233463_m1 and Mm00802100_m1.
   TLSP Taqman gene expression assay (Mm01157588_m1).
   GAPDH Taqman gene expression assay (Hs00266705_g1).
   Non Radioactive Cell Proliferation Assay kit (Promega, Mannheim, Germany).
   Human mast cells (HMC-1).
   Ionomycin calcium salt 1 mM in DMSO (from Sigma Life Science Ref#I3909-1 ml).
   Annexin-V detection kit Life Technologies (Ref: V13241).
1. In Vitro Analysis
1.1 FLAP Expression Levels after Transfection of siRNAs of the Present Invention in Different Cell Lines.

Figure 3:
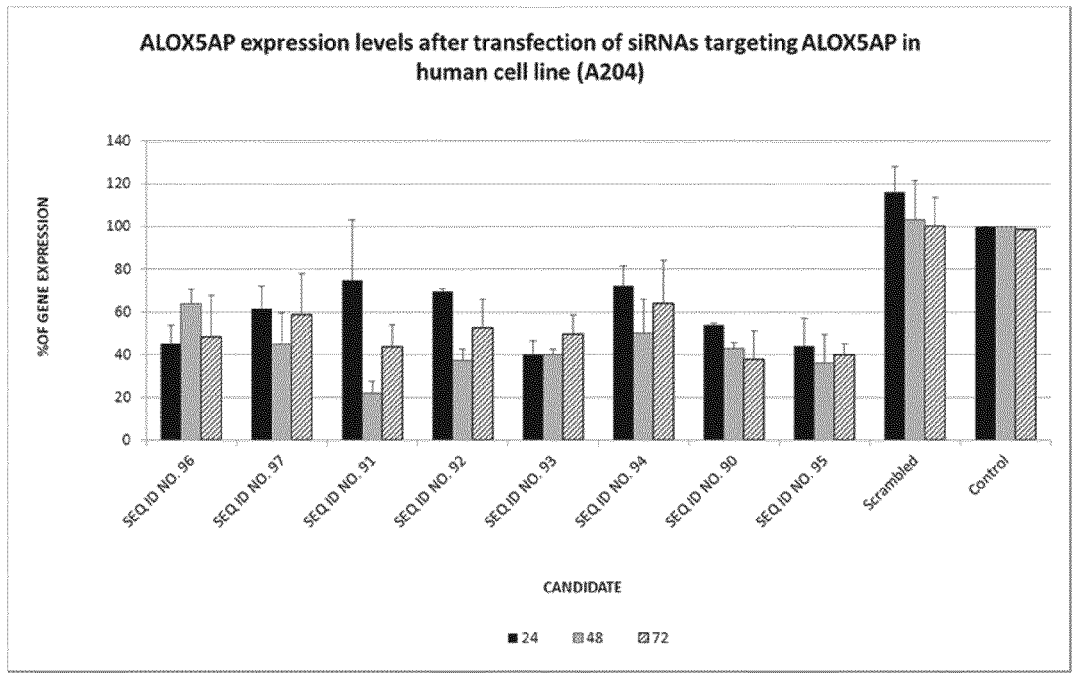
FIG. 3: in vitro ALOX5AP(FLAP) expression levels after transfection of siRNAs targeting ALOX5AP(FLAP) in human cell line A204.
Figure 4:
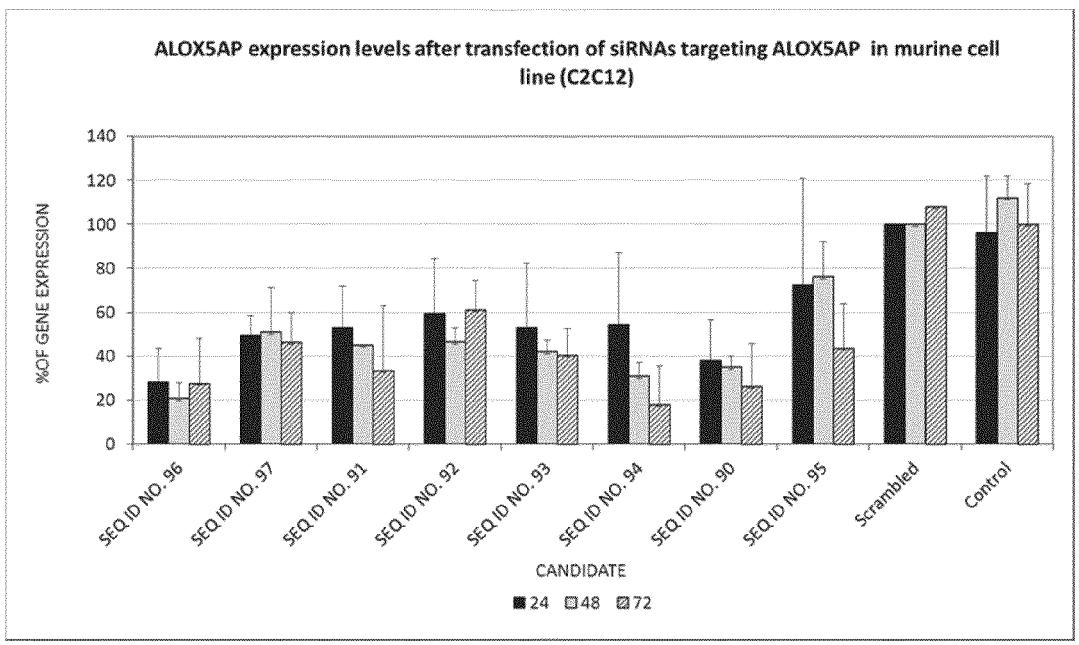
FIG. 4: in vitro ALOX5AP(FLAP) expression levels after transfection of siRNAs targeting ALOX5AP(FLAP) in murine cell line C2Cl2.

In order to demonstrate the silencing effect of the siRNAs of the present invention, in vitro FLAP expression levels were measured after transfection of a selection of siRNAs of the present invention in different cell lines. Human A204 and murine C2Cl2 cells were transfected with 100 nM of SEQ ID NO. 90, SEQ ID NO. 91, SEQ ID NO. 92, SEQ ID NO. 93, SEQ ID NO. 94, SEQ ID NO. 95, SEQ ID NO. 96 and SEQ ID NO. 97 (all these sequences correspond to 19 bp blunt ended dsRNA structures) with Transit TKO and Lipofectamine 2000 respectively as transfection agents. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations in mRNA levels as a consequence of siRNA mechanism of action. RNA levels were quantified by real-time PCR using a relative quantitation method, the Comparative Threshold 2-ΔΔ CT method {Livak and Schmittgen, 2001}. All real time quantitative PCR experiments were performed in triplicate and repeated in three independent experiments. Mean and standard deviation were calculated. As FIG. 3 shows SEQ ID NO. 90, SEQ ID NO. 91, SEQ ID NO. 92, SEQ ID NO. 93, SEQ ID NO. 94, SEQ ID NO. 95, SEQ ID NO. 96 and SEQ ID NO. 97 reduced significantly FLAP mRNA levels approximately 60% in A204 and 60-80% in C2Cl2 (FIG. 4).

1.2 Cellular Viability of Different Cell Lines after Transfection with a siRNA of the Present Invention.

Figure 5:
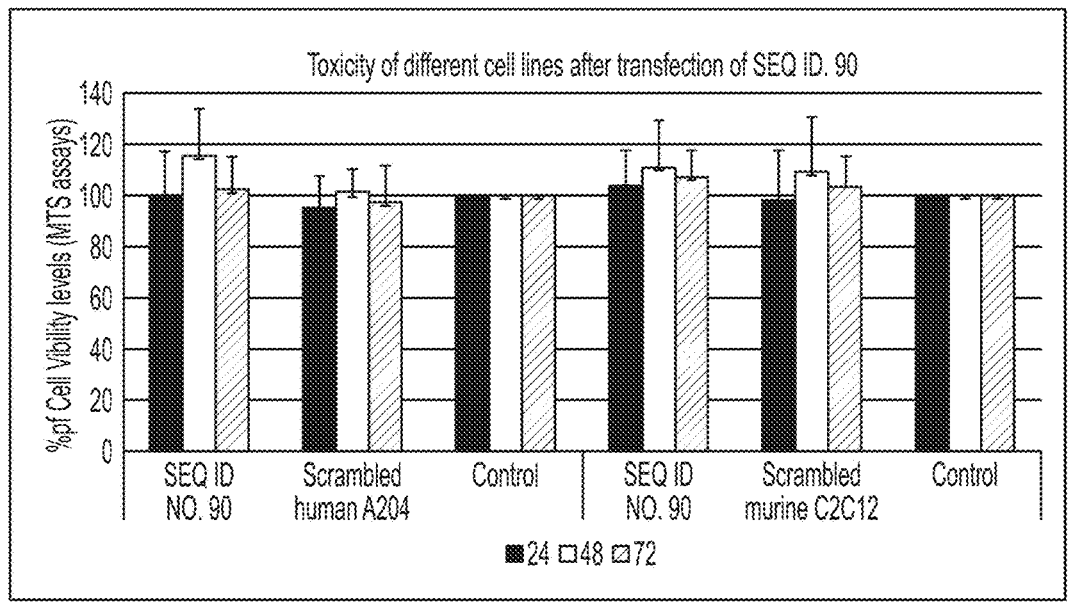
FIG. 5: in vitro toxicity of different cell lines after transfection of SEQ ID NO. 90.

In order to demonstrate the cellular viability of the siRNAs of the present invention, in vitro toxicity levels were measured after transfection of a specific siRNA of the present invention in different cell lines. Human A204 and murine C2Cl2 and J744A.1 cells were transfected with 100 nM of SEQ ID NO. 90 (19 bp blunt ended dsRNA structure) with Transit TKO and Lipofectamine 2000 respectively as transfection agents. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations cell viability levels as a consequence of siRNA transfection. Cell viability was measured using CellTiter 96® Aqueous Non-Radioactive Cell. Proliferation Assay from Promega. This method is based on capacity of living cells (dehydrogenase enzymes) to reduce the MTS tetrazolium compound into formazan product as measured by the amount of 490 nm absorbance. Mean and standard deviation were calculated. As FIG. 5 shows no changes in cell viability levels were found for SEQ ID NO. 90. Therefore, SEQ ID NO. 90 is not toxic and it is safe.

2. In Vivo Analysis

The objective of these examples was to analyze the efficacy of the siRNAs of the present invention, designed to silence expression of FLAP. Specifically, siRNA with SEQ ID NO. 90 (19 bp blunt ended dsRNA structure, SYL116006) to reduce symptoms associated with ocular allergies in a mouse model of ocular allergy induced by ragweed pollen.

Ragweeds are flowering plants in the genus *Ambrosia* in the sunflower family Asteraceae. Ragweed pollen is highly allergenic, generally considered the greatest aeroallergen of all airborne pollens and the prime cause of hay fever worldwide. The National Institute of Environmental Health Science (NIEHS) indicates that ragweed and other weeds such as curly dock, lambs quarters, pigweed, plantain, sheep sorrel and sagebrush are some of the most prolific producers of pollen allergens around the world. This pollen is commonly used in animal models for studying allergic conjunctivitis {Bacsi A. et al 2005}.

The aim of this analysis was to determine if down regulation of FLAP by ocular instillation of compounds of the present invention, specifically SEQ ID NO. 90 (SYL116006) alleviates the symptoms caused by ragweed pollen-induced ocular allergy in mice.

We have analysed whether FLAP is expressed in the mouse eye and if its expression is up-regulated in response to ragweed pollen-induced ocular allergy. We have also assessed the effect of silencing the expression of FLAP using locally applied SEQ ID NO. 90 (SYL116006) on allergy response in the above mentioned mouse model. For this purpose the following parameters have been analyzed:

Clinical signs in response to allergy induction: typical ocular signs of allergic conjunctivitis include itching, eyelid swelling, conjunctival swelling (chemosis), and mucus deposition. Mucus associated to ocular allergies is profuse, stringy and even sticky. Alterations to the conjunctiva usually cause the bulbar conjunctiva to take on a "glassy" appearance and the colouring of the palpebral conjunctiva is more pink than red with a frequently milky appearance.

Number of local mast cells: minutes after allergic stimulation conjunctival mast cells degranulate; the release of inflammatory mediators attracts more mast cells that migrate from deeper layers of the conjunctiva.

Local infiltration of eosinophils: infiltration of inflammatory cells to the conjunctiva occurs hours after allergen exposure and is part of the late response to allergens. Although several different types of cells migrate to the conjunctiva the main type are eosinophils.

Expression changes in molecular biomarkers related to allergy:

PDK1: Mast cells function is strictly regulated through changes of ion channel activity and several signaling pathways. Activation of mast cells in response to allergens causes changes in membrane permeability to ions. Entrance of $Ca^{2+}$ to the cells activates phosphatidylinositol 3 kinase (PI3K). Activation of the PI3K pathway includes activation of phospho-inositide-dependent kinase (PDK1) which in turn phosphorylates downstream targets of PI3K such as PKB/Akt, SGK and PKC. These kinases are responsible for the activation of calcium channels to mobilize intracellular calcium stores and activate mast cell degranulation {Shumilina E, et al. 2010}.

2.1 Methods

A. Animals and Animal Procedures 2.1.1 Test system characterisation

TABLE 1

Test system characterisation

| | |
|---|---|
| Species: | Mouse |
| Strain: | BALB-C |
| Sex: | Female |
| Colour: | White |
| Rationale for selection of species/strain: | This strain has been previously been established as a good model for ocular allergies {Bacsi A. et al 2005}. |
| Approx. age of the animals at the beginning of the study: | 8-10 weeks |

A further advantage of the siRNAs of the present invention is that SEQ ID NO. 1-SEQ ID NO. 20 correspond to highly conserved regions of the FLAP gene, throughout different animal sequences. In fact, these sequences are identical between human and mouse, making this animal model especially suitable for the study of for ocular allergies.

2.1.2 Induction of Allergy

Allergic conjunctivitis was induced by immunizing the animals with a mixture of 50 µg ragweed (Rw) pollen in 0.25 ml alum by intraperitoneal injection on day 1. The immunization solution was prepared immediately prior to administration and was protected from light at all times. Ten days after immunization 1.25 mg of Rw pollen was topically instilled into each eye. Administrations were performed in a dose volume of 5 µL/eye. This procedure was adapted from a standard preexisting published protocol known to an expert in the field and validated prior to assessing the efficacy of the siRNAs {Magone M. T. et al 1998}.

2.1.3 Test Item Administration

Figure 6:
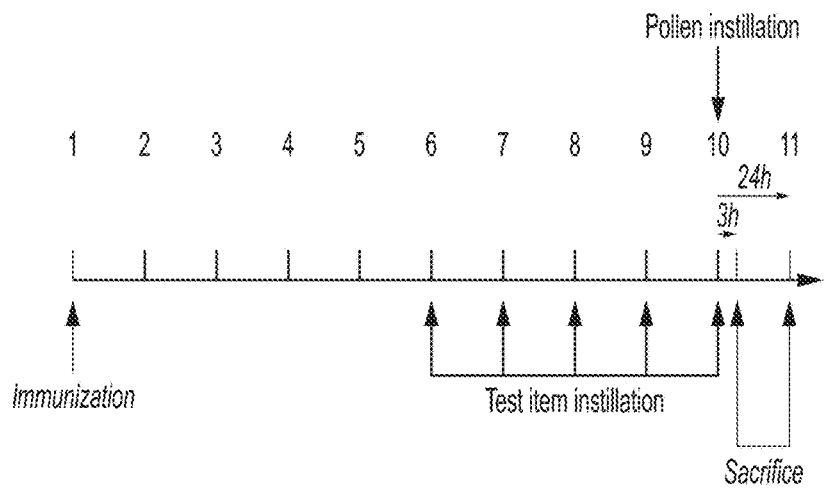
FIG. 6: Schedule of the in vivo assay.

The test item was applied by the topical ocular route to both eyes of the animals once a day over a period of 5 days starting on day 6 (FIG. 6). A separate group of animals was administered with vehicle (PBS) and served as control. Administrations were performed in a dose volume of 5 µL/eye.

2.1.4 Clinical Observations and Collection of Samples

General health status of animals was monitored daily from first administration until sacrifice. Mice were examined for clinical signs of hypersensitivity prior to instillation of topical ocular pollen and at different time-points up to 24 h after pollen instillation. Conjunctival chemosis and injection, lid edema, discharge and tearing were graded on a scale 0-3. Clinical scoring was performed by an experimented observer blind to the experimental condition. Animals were sacrificed either 3 or 24 h after allergy challenge. Following sacrifice eyes, lymph nodes were isolated and either processed for histology.

2.1.5 Histopathology

The exenterated eyes were immersed in 10% formaline (½₀ volume) for 24 h hours, then the formaline was removed with several washes of phosphate buffer 0.1M and maintained almost 24 h hours in this buffer. Samples were dehydrated by incubating them in increasing concentrations of ethanol, and were thereafter embedded in low melting paraffin in a tissue processor (Leica T P 1020, Cat. no—0704 37101, Leica Microsystems, Nussloch, Germany). Samples were cut in a microtome to obtain sections of 2 µm that were thereafter stained with either toludine blue to count the number of mast cells or with hematoxyline-eosine to assess eosinophil infiltration.

2.1.6 RNA Isolation and Retrotranscription

Total RNA was isolated from whole eyes, spleen or lymph nodes using RNeasy RNA extraction kit (Invitrogen, CA, USA). 4 µg of total RNA were retrotranscribed using High-Capacity cDNA Archive kit (Applied Biosystems, Inc., Foster City, Calif., USA) according to the manufacturer's instructions.

2.1.7 qPCR qPCR was performed using Stepone plus detection system (Applied Biosystems). 500 nanograms of each sample were amplified in a TaqMan 2× Universal Master Mix under the following conditions: 95° C. for 10 min, followed by 40 cycles of 95° C. for 15 s and 60° C. for 1 min. All qPCR amplifications were performed in triplicate and repeated in at least two independent experiments, always including reverse transcription controls and no template controls. FLAP and PDK1 mRNA levels were analyzed by qPCR using the ΔΔCT method of relative quantification using 18S gene as internal standard {Livak and Schmittgen, 2001}.

2.2 Results 2.2.1 Expression of FLAP in Mouse Eye and Induction in Response to Ocular Allergy.

Figure 7:
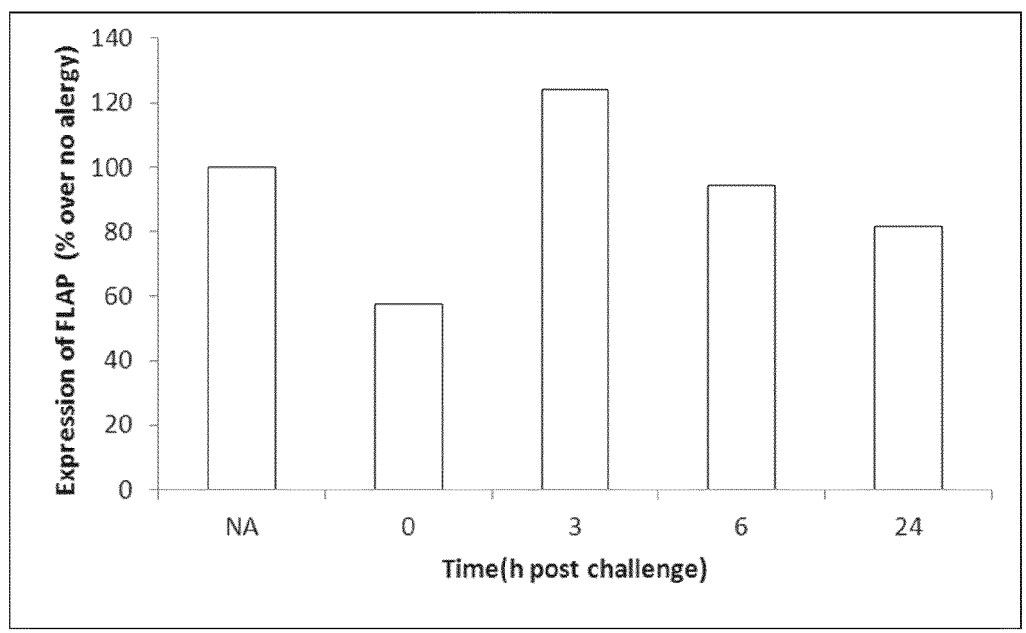
FIG. 7: Levels of FLAP mRNA in mouse whole eye at different times following induction of ocular allergy. NA: no allergy.

Expression of FLAP was assessed in eyes of mice at different time points after induction of allergy as mentioned in the methods section. FIG. 7 shows that FLAP is present in the eye and that its expression is rapidly up-regulated in response to the allergic challenge; approximately a 1.3-fold increase in FLAP mRNA levels was observed 3 h after administration of ragweed pollen. 6 h post challenge levels of FLAP were back to basal levels.

Figure 8:
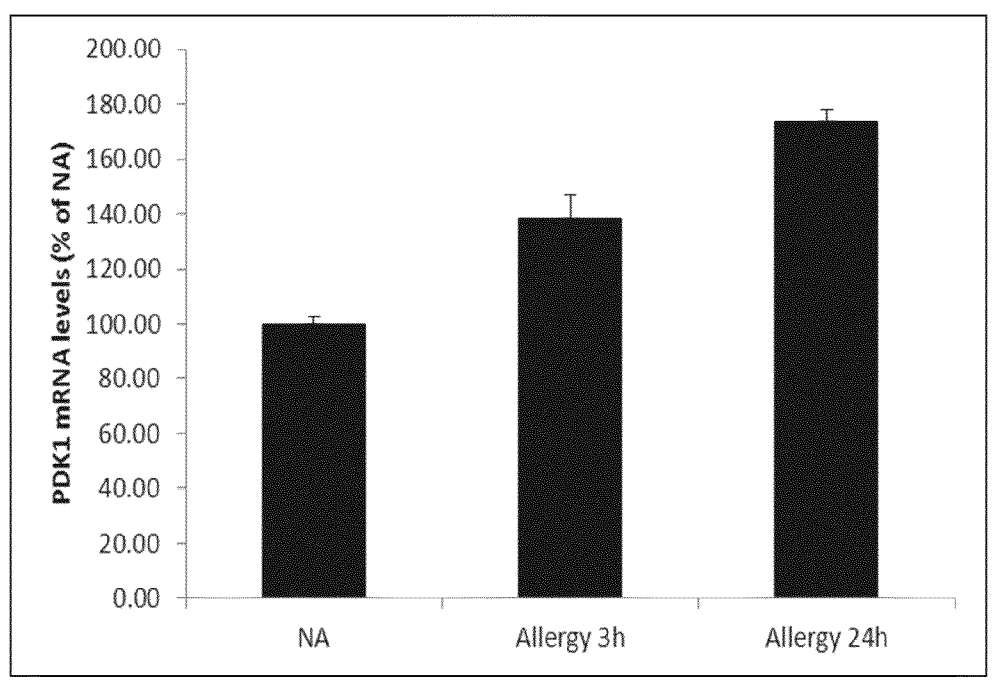
FIG. 8: mRNA levels of PDK1 in a mouse model of ragweed-pollen induced allergy. mRNA levels are expressed as percentage of the levels observed prior to induction of allergy.
Figure 9:
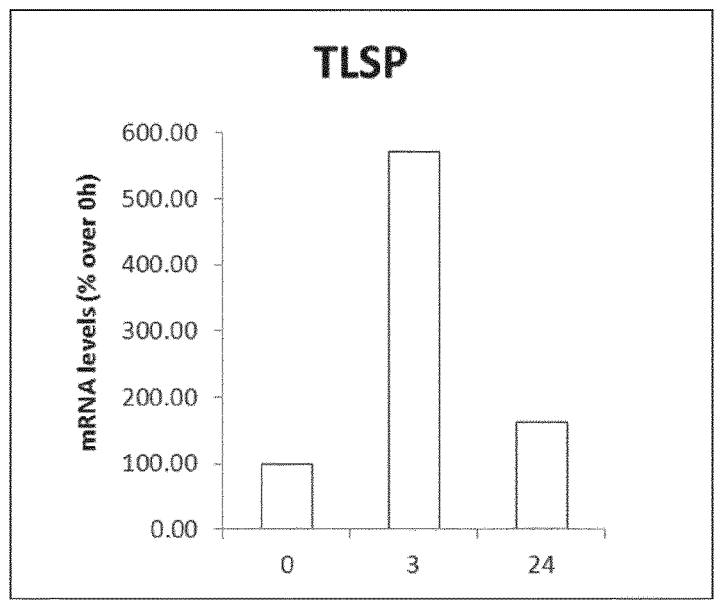
FIG. 9: mRNA levels of TLSP in a mouse model of ragweed-pollen induced allergy. mRNA levels are expressed as percentage of the levels observed prior to induction of allergy.

2.2.1 Assessment of Expression of Allergy Biomarkers in Response to Ocular Allergy.

mRNA levels of PDK1 were studied at different time-points following induction of ocular allergy by instillation of ragweed pollen in pre-sensitized mice. As shown in FIG. 8 PDK1 mRNA levels increased over time in response to allergy challenge reaching maximum levels of approximately 1.7 times basal levels 24 h post induction.

mRNA levels of TLSP were also studied at different time-points following induction of ocular allergy by instillation of ragweed pollen in pre-sensitized mice. A significant induction in TLSP was observed 3 h post challenge. 24 h after induction mRNA levels of TLSP were almost returned to basal levels (FIG. 9).

2.2.2 Efficacy of SEQ ID NO. 90 (SYL116006) in a Mouse Model of Ocular Allergy

Figure 10:
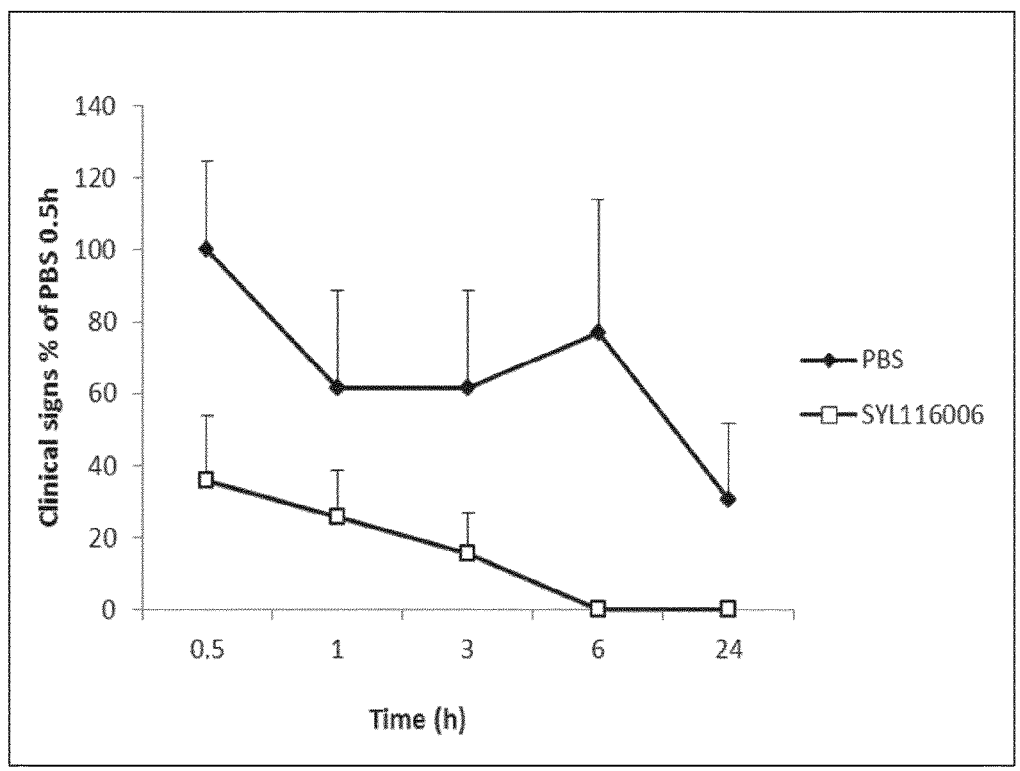
FIG. 10: Ocular clinical signs indicative of ocular allergy. Mice were observed 0.5, 1, 3, 6 and 24 h after induction of ocular allergy. Clinical signs were assessed by grading the following parameters on a scale 0-3: conjunctival chemosis and injection, hyperemia, lid edema, discharge and tearing. Data are expressed as percentage of the clinical scoring at 0.5 h after induction of allergy of the PBS treated group and represent means±s.e.m of 16 animals for PBS and 24 animals for the SEQ ID NO. 90 (SYL116006) treated group.

Two groups of animals were intraperitoneally (IP) injected with a dose of ragweed pollen adsorbed on alum as mentioned in the methods section. Five days after the IP injection one group (A, n=16) received an ocular instillation/day of PBS over a period of five days, the other group received SEQ ID NO. 90 (19 bp blunt ended dsRNA structure, SYL116006) at the dose of 450 µg/eye/day (low dose) (B, n=24) during the same period of time. Animals were examined for symptoms related to ocular allergy 0.5, 1, 3, 6 and 24 h after ocular instillation of pollen. As shown in FIG. 10 treatment with SEQ ID NO. 90 (SYL116006) significantly reduced the clinical signs of allergy. It is particularly interesting that no clinical signs were observed 6 h post-challenge in the group of animals treated with SEQ ID NO. 90 (SYL116006); this means that SEQ ID NO. 90 (SYL116006) was not only able to reduce the intensity of clinical signs but also the duration. Further analysis of the clinical signs indicated that SEQ ID NO. 90 (SYL116006) had an especially potent effect on palpebral edema, tearing and ocular discharge.

Infiltration of mast cells was assessed in palpebral and bulbar conjunctiva 3 h after induction of ocular allergy. SEQ ID NO. 90 (SYL116006) administered at the dose of 475 µg/eye/day caused a significant reduction in the number of mast cells infiltrating both the palpebral and bulbar conjunctiva (FIG. 11).

Eosinophil infiltration was assessed in conjunctiva 3 h and 24 h post-challenge. Again, a significant decrease in infiltrating eosinophils was observed in response to the high dose of SEQ ID NO. 90 (SYL116006) in both regions of the conjunctiva (FIG. 12).

Analysis of mRNA levels of the target gene (FLAP) in eye in response to treatment with SEQ ID NO. 90 (SYL116006). As shown in FIG. 13 there was a significant reduction in the levels of FLAP mRNA 3 h and 24 h after allergy induction in the animals pre-treated with SEQ ID NO. 90 (SYL116006).

Analysis of the allergy biomarker PDK1 in eye indicated that, as expected, there was an increase in mRNA levels of PDK1 24 h after induction of allergy. Pretreatment with SEQ ID NO. 90 (SYL116006) inhibited the induction of this gene in response to ragweed pollen (FIG. 14).

REFERENCES

Angaji S. A, Hedayati S. S, Poor R. H, et al. "Application of RNA interference in treating human diseases" *J Genet.* 2010. Vol. 89. 4. 527-37.

Bair A M, Turman M V, Vaine C A, et al. "The nuclear membrane leukotriene synthetic complex is a signal integrator and transducer". *Mol Biol Cell* 2012; 23:4456-4464.

Bacsi A, Dharajiya N, Choudhury B K, Sur S, Boldogh I. "Effect of pollen-mediated oxidative stress on immediate hypersensitivity reactions and late-phase inflammation in allergic conjunctivitis." *J Allergy Clin Immunol.* 2005 October; 116(4):836-43.

Bramsen J. B., Laursen M. B., Nielsen A. F., et al. "A large-scale chemical modification screen identifies design rules to generate siRNAs with high activity, high stability and low toxicity" *Nucleic Acids Res* 2009 Vol. 37 Issue: 9 Pages: 2867-81.

Cerutti, L., N. Mian, et al. "Domains in gene silencing and cell differentiation proteins: the novel PAZ domain and redefinition of the Piwi domain." *Trends Biochem Sci.* 2000 25(10): 481-2.

Collins, R. E. and X. Cheng. "Structural domains in RNAi." *FEBS Lett.* 2005; 579(26): 5841-9.

Chang C. I, Kim H. A, Dua P, Kim S, et al. "Structural Diversity Repertoire of Gene Silencing Small Interfering RNAs" *Nucleic Acid Ther.* 2011. Vol. 21. 3. 125-31.

Deleavey G. F and Damha M. J. "Designing chemically modified oligonucleotides for targeted gene silencing". *Chem Biol.* 2012; Vol. 19. 8. 937-54.

Diamant Z, Timmers M C, van der Veen H, et al. "The effect of MK-0591, a novel 5-lipoxygenase activating protein inhibitor, on leukotriene biosynthesis and allergen-induced airway responses in asthmatic subjects in vivo". *J Allergy Clin Immunol* 1995; 95:42-51.

Dixon R A, Diehl R E, Opas E, et al. "Requirement of a 5-lipoxygenase-activating protein for leukotriene synthesis". *Nature* 1990; 343:282-284.

Doench, J. G. Sharp, P. A. "specificity of microRNA target selection in translational repression" *Genes Dev.* 2004; 18, 504-511.

Elbashir, S. M., W. Lendeckel, et al. "RNA interference is mediated by 21- and 22-nucleotide RNAs." *Genes Dev* 2001; 15(2): 188-200.

Ferguson A D, McKeever B M, Xu S, Wisniewski D, et al. "Crystal structure of inhibitor-bound human 5-lipoxygenase-activating protein". (July 2007) *Science* 317 (5837): 510-2.

Fire, A., S. Xu, et al. "Potent and specific genetic interference by double-stranded RNA in *Caenorhabditis elegans.*" *Nature* 1998; 391(6669): 806-11.

Galli S J, and Tsai M. "IgE and mast cells in allergic disease". *Nat Med* 2012; 18:693-704.

Hofmann B, Steinhilber D. "5-Lipoxygenase inhibitors: a review of recent patents (2010-2012)" *Expert Opin Ther Pat.* 2013 July; 23(7):895-909.

Kari O. and Saari K M. "Updates in the treatment of ocular allergies". *Journal of Asthma and Allergy* 2010: 3 149-158.

Key B. Allergy and allergic diseases. Part I. *N. Engl J Med.* 2001; 344:30-37.

Kim D. H., Behlke M. A., Rose S. D., et al. "Synthetic dsRNA Dicer substrates enhance RNAi potency and efficacy" *Nat Biotechnol* 2005; Vol. 23 Issue: 2 Pages: 222-6.

Kornbrust D, Cavagnaro J, Levin A, et al. "Oligo safety working group exaggerated pharmacology subcommittee consensus document" *Nucleic Acid Ther* 2013 Vol. 23, 1, Pag: 21-8.

La Rosa M, Lionetti E, Reibaldi M, et al. "Allergic conjunctivitis: a comprehensive review of the literature" *Italian Journal of Pediatrics* 2013, 39:18.

Lewis, B. P., Shih I. et al. "prediction of mammalian micro RNA targets" *Cell* 115:787-798; 2003.

Liu, J., M. A. Carmell, et al. "Argonaute2 is the catalytic engine of mammalian RNAi." *Science* 2004; 305(5689): 1437-41.

Livak K. J. and Schmittgen T. D., "Analysis of relative gene expression data using real-time quantitative PCR and the 2(-Delta Delta C(T)) Method" Methods. 2001; Vol: 25, Issue: 4, Pages: 402-8.

Ma, J. B., Y. R. Yuan, et al. "Structural basis for 5'-end-specific recognition of guide RNA by the *A. fulgidus* Piwi protein." *Nature* 2005; 434(7033): 666-70.

Mancini J. A, Abramovitz M, Cox M. E, et al. "5-lipoxygenase-activating protein is an arachidonate binding protein." *Federation of European Biochemical Societies* 1993 318:277-281.

Maniatis, T., et al., "Molecular Cloning: A Laboratory Manual". *Cold Spring Harbor Laboratory,* 1982, at pages 387-389.

Magone M T, Chan C C, Rizzo L V, et al. "A novel murine model of allergic conjunctivitis". *Clin Immunol Immunopathol* 1998; 87:75-84.

Nykanen, A., B. Haley, et al. "ATP requirements and small interfering RNA structure in the RNA interference pathway." *Cell* 2001; 107(3): 309-21.

Ono S J, Abelson M B. "Allergic conjunctivitis: update on pathophysiology and prospects for future treatment" *J. Allergy Clin. Immunol.* 2005, 75(1), 1 18-122.

Parrish, S. J. Fleenor, et al. "Functional anatomy of a dsRNA trigger: differential requirement for the two trigger strands in RNA interference." *Mol Cell* 2000; 6(5): 1077-87.

Plewako H, Holmberg K, Oancea I, Rak S. "Increased expression of lipoxygenase enzymes during pollen season in nasal biopsies of pollen-allergic patients" *Allergy* 2006 June; 61(6):725-30.

Popescu F D. "Antisense- and RNA interference-based therapeutic strategies in allergy" *J Cell Mol Med.* 2005 October-December; 9(4):840-53.

Rand, T. A., S. Petersen, et al. "Argonaute2 cleaves the anti-guide strand of siRNA during RISC activation." *Cell* 2005; 123(4): 621-9.

Sacre Hazouri J A. "Leukotrien antagonists in the treatment of allergic rhinitis and comorbidities" *Rev Alerg Mex.* 2008 July-August; 55(4):164-75.

Sanghvi Y. S. "A status update of modified oligonucleotides for chemotherapeutics applications" *Curr Protoc Nucleic Acid Chem.* 2011; Vol. 4. 4 1 1-22.

Shumilina E, Zemtsova I M, Heise N, et al. "Phosphoinositide-dependent kinase PDK1 in the regulation of Ca2+ entry into mast cells". *Cell Physiol Biochem* 2010; 26:699-706.

Song, J. J., S. K. Smith, et al. "Crystal structure of Argonaute and its implications for RISC slicer activity." *Science* 2004; 305(5689): 1434-7.

Suzuki M, Zheng X, Zhang X, et al. "Inhibition of allergic responses by CD40 gene silencing" *Allergy.* 2009 March; 64(3):387-97.

Suzuki M, Zheng X, Zhang X, et al. "A novel allergen-specific therapy for allergy using CD40-silenced dendritic cells" *J Allergy Clin Immunol.* 2010 March; 125(3):737-43.

Walton S. P, Wu M, Gredell J. A and Chan C. "Designing highly active siRNAs for therapeutic applications" *FEBS J.* 2010. Vol. 277. 23. 4806-13.

Woods J. W, Evans J. F, Ethier D, et al. "5-Lipoxygenase and 5-Lipoxygenase-activating Protein Are Localized in the Nuclear Envelope of Activated Human Leukocytes" *J. Exp. Med. The Rockefeller University Press* 1993 Vol. 178. 1935-1946.

The invention claimed is:

1. A method of treating ocular allergy and/or conjunctivitis characterised by increased expression and/or activity of FLAP in a subject in need thereof, the method comprising: topically administering to the corneal surface of the eye of the subject an amount of an siRNA molecule which specifically targets at least one sequence selected from SEQ ID NO. 1 to SEQ ID NO. 89 effective to decrease the expression and/or activity of FLAP in cells of the eye and to treat the ocular allergy and/or conjunctivitis.

2. The method according to claim 1, wherein said ocular allergy and/or conjunctivitis is selected from the group consisting of seasonal allergic conjunctivitis, perennial allergic conjunctivitis, vernal keratoconjunctivitis, atopic keratoconjunctivitis, giant papillary conjunctivitis, dry eye syndrome and combinations thereof.

3. The method according to claim 1, wherein said siRNA comprises a 19 nucleotide double-stranded region.

4. The method according to claim 3, wherein said siRNA is blunt-ended.

5. The method according to claim 4, wherein said siRNA includes at least one sequence selected from SEQ ID NO. 90 to SEQ ID NO. 178.

6. The method according to claim 3, wherein at least one nucleotide of said siRNA molecule comprises a chemical modification.

7. The method according to claim 6, wherein said chemical modification is selected from the group consisting of 2'-O-methylation; substitution of uracyl ribose nucleotides with deoxythymidine nucleotides; and combinations thereof.

8. The method according to claim 6, wherein said chemical modification is on the sense strand, the antisense strand, or on both the sense and the antisense strand.

9. The method according to claim 5, wherein the siRNA includes the nucleotide sequence set forth in any one of SEQ ID NO. 90 to SEQ ID NO. 97.

10. The method according to claim 9, wherein the siRNA includes the nucleotide sequence set forth in SEQ ID NO. 90.

11. The method of claim 1, wherein said siRNA molecule is a double stranded, blunt-ended siRNA molecule consisting of 19 nucleotides, which comprises at least one sequence selected from SEQ ID NO. 90 to SEQ ID NO. 178.

12. The method according to claim 11, wherein said ocular allergy and/or conjunctivitis is selected from the group consisting of seasonal allergic conjunctivitis, perennial allergic conjunctivitis, vernal keratoconjunctivitis, atopic keratoconjunctivitis, giant papillary conjunctivitis, dry eye syndrome and combinations thereof.

13. The method according to claim 11, wherein at least one nucleotide of said siRNA molecule comprises a chemical modification.

14. The method according to claim 13, wherein said chemical modification is selected from the group consisting of 2'-O-methylation; substitution of uracyl ribose nucleotides with deoxythymidine nucleotides; and combinations thereof.

15. The method according to claim 14, wherein said chemical modification is on the sense strand, the antisense strand, or on both the sense and the antisense strand.

* * * * *